United States Patent
Ko et al.

(10) Patent No.: US 11,592,655 B2
(45) Date of Patent: Feb. 28, 2023

(54) MICROSCOPE MADE WITH CMOS CAMERA(S)

(71) Applicant: LIGHTech Fiberoptics, Inc., San Leandro, CA (US)

(72) Inventors: Chun-Ming Ko, San Ramon, CA (US); Jianhung Tsai, Taipei (TW)

(73) Assignee: LIGHTech Fiberoptics, Inc., San Leandro, CA (US)

( * ) Notice: Subject to any disclaimer, the term of this patent is extended or adjusted under 35 U.S.C. 154(b) by 0 days.

(21) Appl. No.: 17/731,392

(22) Filed: Apr. 28, 2022

(65) Prior Publication Data
US 2022/0260824 A1 Aug. 18, 2022

Related U.S. Application Data

(62) Division of application No. 16/505,951, filed on Jul. 9, 2019, now Pat. No. 11,340,441.

(51) Int. Cl.
*H04N 13/15* (2018.01)
*G02B 21/36* (2006.01)
(Continued)

(52) U.S. Cl.
CPC ............ *G02B 21/362* (2013.01); *A61B 90/20* (2016.02); *A61B 90/37* (2016.02);
(Continued)

(58) Field of Classification Search
CPC ....... G02B 21/362; A61B 90/20; A61B 90/37; G06T 7/80; G06T 7/30; G06T 7/97;
(Continued)

(56) References Cited

U.S. PATENT DOCUMENTS 5,867,210 A 2/1999 Rod
6,326,995 B1 12/2001 Palm et al.
(Continued)

FOREIGN PATENT DOCUMENTS

CN 106210697 12/2016

OTHER PUBLICATIONS

U.S. Notice of Allowance, U.S. Appl. No. 16/505,951, Applicant: Ko et al., dated Feb. 4, 2022, 7 pages.
(Continued)

*Primary Examiner* — Nguyen T Truong
(74) *Attorney, Agent, or Firm* — Saile Ackerman LLC; Stephen B. Ackerman; Billy Knowles

(57) ABSTRACT

A medical/surgical microscope with two cameras configured to capture two dimensional images of specimens being observed. The medical/surgical microscope is secured to a control apparatus configured to adjust toe-in of the two cameras to insure the convergence of the images. The medical/surgical microscope includes a computer system with a non-transitory memory apparatus for storing computer program code configured for digitally rendering real-world medical/surgical images. The medical/surgical microscope has an illumination system with controls for focusing and regulating the lighting of a specimen. The medical/surgical microscope is configured for real-time video display with the function of recording and broadcasting simultaneously during surgery.

15 Claims, 24 Drawing Sheets

(51) Int. Cl.

| | |
|---|---|
| *H04N 5/225* | (2006.01) |
| *H04N 5/232* | (2006.01) |
| *G06T 5/00* | (2006.01) |
| *H04N 13/133* | (2018.01) |
| *H04N 13/156* | (2018.01) |
| *G06T 5/50* | (2006.01) |
| *G06T 1/20* | (2006.01) |
| *G06T 7/80* | (2017.01) |
| *G06T 7/30* | (2017.01) |
| *G06T 7/90* | (2017.01) |
| *G06T 7/00* | (2017.01) |
| *G06T 3/00* | (2006.01) |
| *H04N 13/239* | (2018.01) |
| *G06T 3/40* | (2006.01) |
| *G02B 21/00* | (2006.01) |
| *G02B 21/06* | (2006.01) |
| *A61B 90/20* | (2016.01) |
| *A61B 90/00* | (2016.01) |

(52) U.S. Cl.
CPC ......... *G02B 21/0012* (2013.01); *G02B 21/06* (2013.01); *G02B 21/361* (2013.01); *G06T 1/20* (2013.01); *G06T 3/0068* (2013.01); *G06T 3/0093* (2013.01); *G06T 3/40* (2013.01); *G06T 5/006* (2013.01); *G06T 5/50* (2013.01); *G06T 7/30* (2017.01); *G06T 7/80* (2017.01); *G06T 7/90* (2017.01); *G06T 7/97* (2017.01); *H04N 5/2253* (2013.01); *H04N 5/2254* (2013.01); *H04N 5/2256* (2013.01); *H04N 5/23229* (2013.01); *H04N 5/23299* (2018.08); *H04N 13/133* (2018.05); *H04N 13/15* (2018.05); *H04N 13/156* (2018.05); *H04N 13/239* (2018.05); *A61B 2090/367* (2016.02); *A61B 2090/371* (2016.02); *G06T 2207/10012* (2013.01); *G06T 2207/10056* (2013.01); *G06T 2207/20212* (2013.01); *G06T 2207/30004* (2013.01)

(58) Field of Classification Search
CPC ........ G06T 7/90; H04N 13/15; H04N 13/156; H04N 13/239; H04N 13/133
USPC .......................................................... 348/79
See application file for complete search history.

(56) References Cited

U.S. PATENT DOCUMENTS

| | | |
|---|---|---|
| 6,483,948 B1 | 11/2002 | Spink et al. |
| 8,339,447 B2 | 12/2012 | Riederer |
| 10,019,819 B2 | 7/2018 | Tripathi et al. |
| 10,091,513 B2 | 10/2018 | Kwon et al. |
| 11,340,441 B2 | 5/2022 | Ko et al. |
| 2007/0188603 A1 | 8/2007 | Riederer et al. |
| 2016/0191887 A1 | 6/2016 | Casas |
| 2017/0115477 A1 | 4/2017 | Kiening et al. |
| 2017/0273559 A1 | 9/2017 | Takahashi et al. |
| 2017/0293129 A1 | 10/2017 | Hatakeyama et al. |
| 2017/0351072 A1 | 12/2017 | Ku et al. |
| 2018/0303574 A1 | 10/2018 | Ramirez Luna |
| 2018/0368656 A1 | 12/2018 | Austin |

OTHER PUBLICATIONS

U.S. Office Action, U.S. Appl. No. 16/505,951, Applicant: Ko et al., dated Jun. 7, 2021, 21 pages.

"Towards Hardware Stereoscopic 3D Reconstruction, A Real-Time FPGA Computation of the Disparity Map," by Hadjitheophanous, et al., 2010 Design, Automation & Test in Europe Conference & Exhibition, Mar. 2010, pp. 1743-1748.

"Dual Lens 3D Steroscopic Microscope for Surgery," by I-Chun Lee et all., Sages Abstract Archives, Society of American Gastrointestinal and Endoscopic Surgeons, 2016, found Dec. 28, 2018 at: https://www.sages.org/meetings/annual-meeting/abstracts-archives/... dual-lens-3d-stereoscopic-microscope-for-surgery/.

"A 3D reconstruction from real-time stereoscopic images using GPU," by Gomez-Balderas J.E. et al., 2013 Conference on Design and Architectures for Signal and Image Processing, Oct. 8-10, 2013, 6 pgs.

DRE Veterinary, "DRE Maxx Luxx LED Surgery Light," Apr. 15, 2013, pp. 1-5, Product ID: 12160, Found: https://www.dreveterinary.com/veterinary-equipment/equine-equipment/dre-maxx-luxx-led.

"Keystone Correction for Stereoscopic Cinematography," by Feng Liu et al., 2012 IEEE Computer Society Conference on Computer Vision and Pattern Recognition Workshops, Jun. 16-21, 2012, pp. 1-7.

"Computational imaging for 3D micrographs with 10-depth-of-field enhancement," by Guillem Carles et al., Mar. 7, 2017, DOI: 1117/2 1201611. 006749, Found: Apr. 2, 2019, 6 pgs.

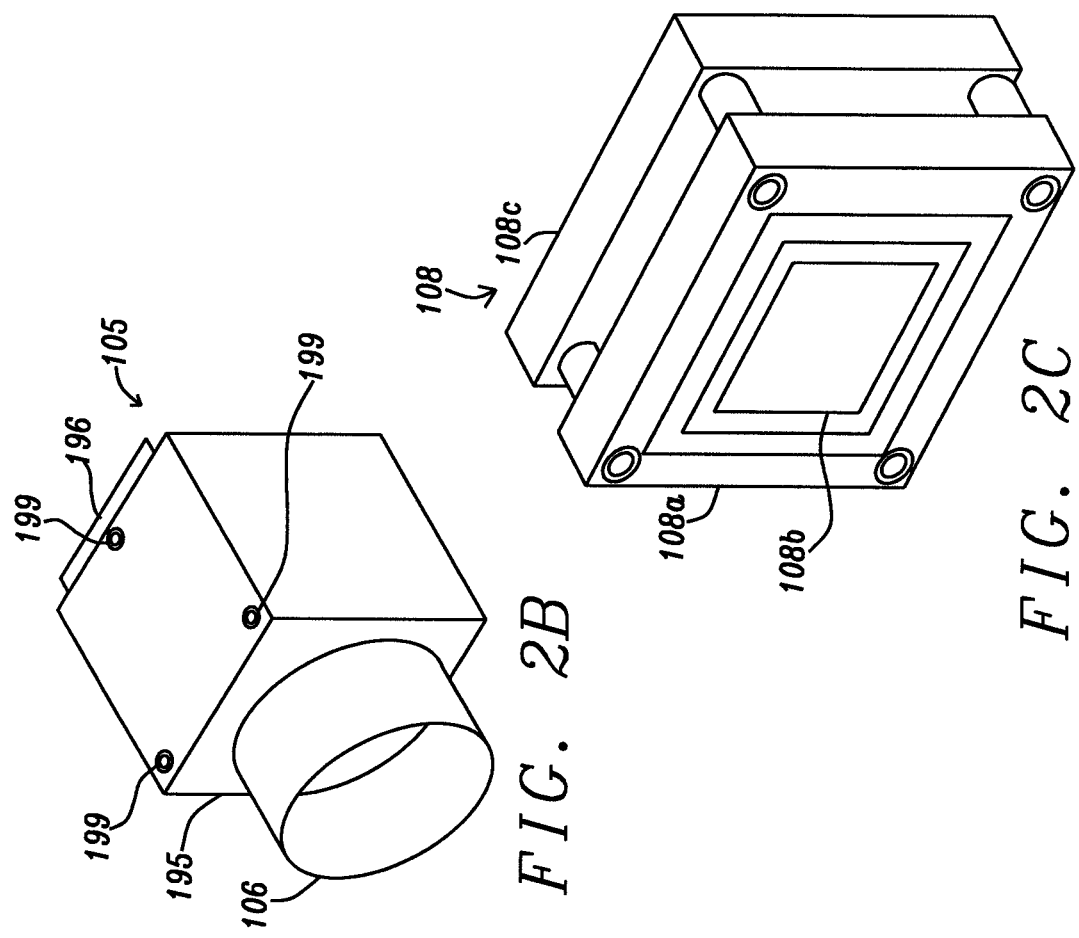
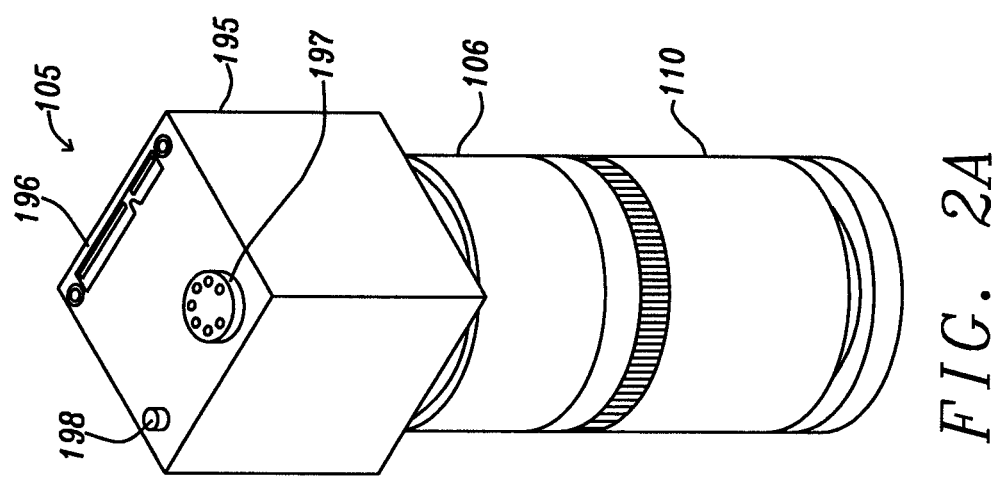

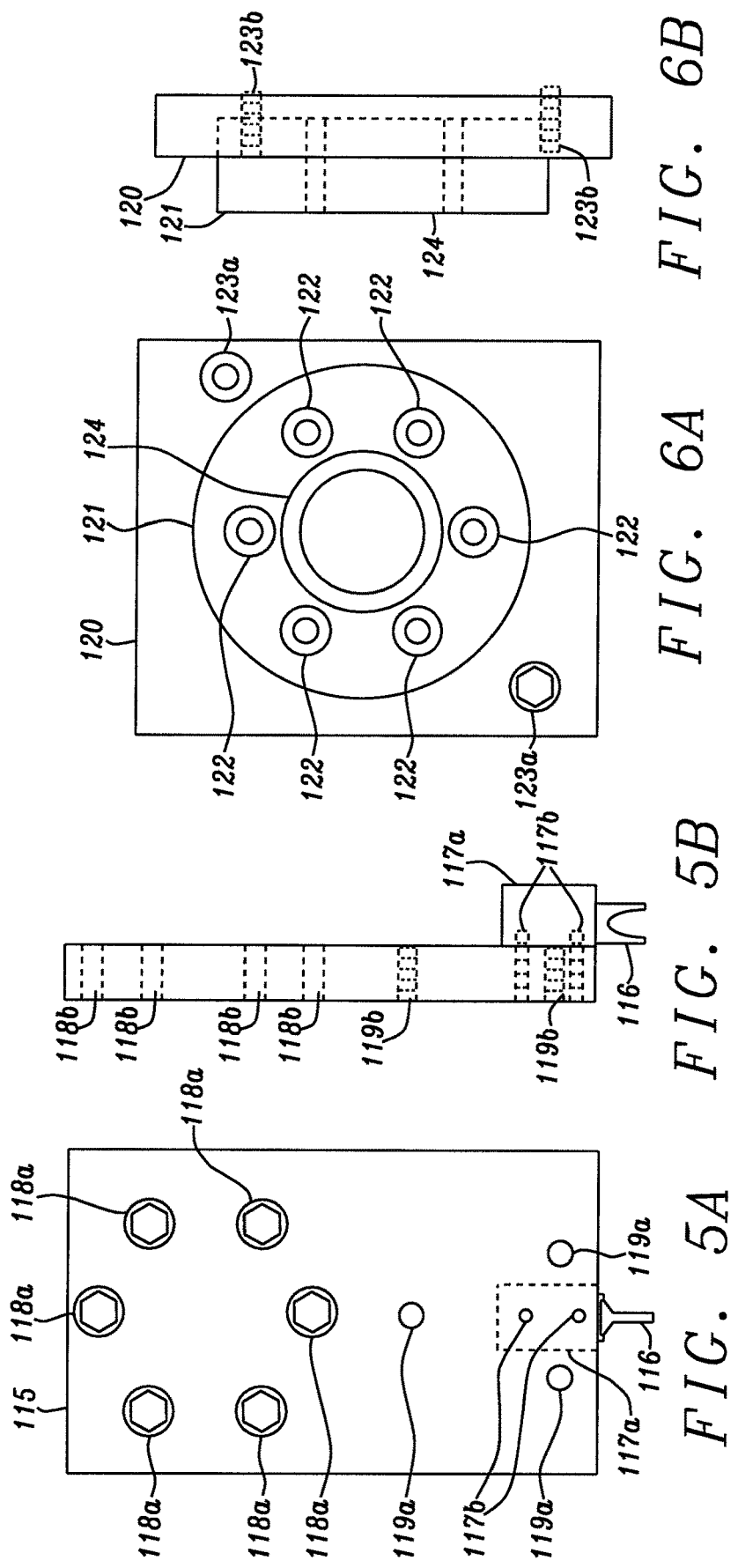

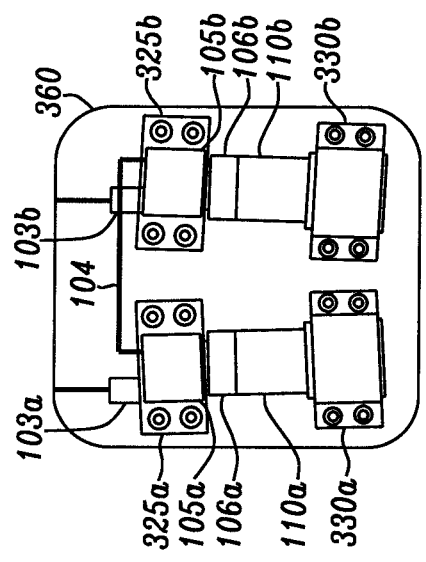
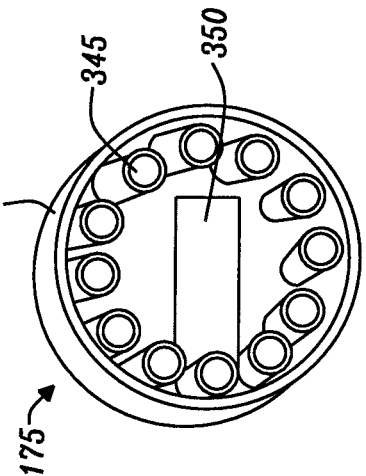
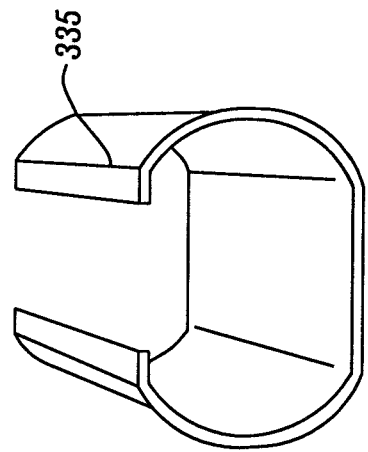
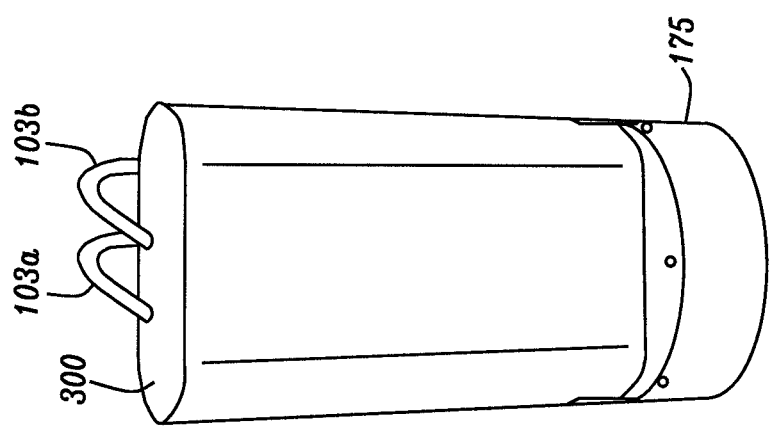

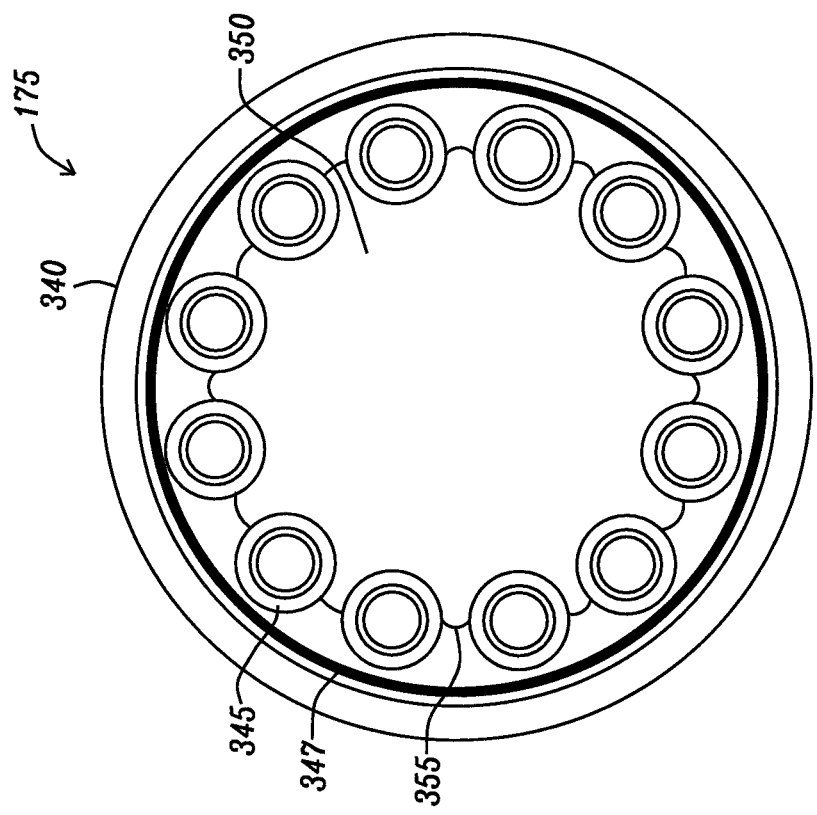
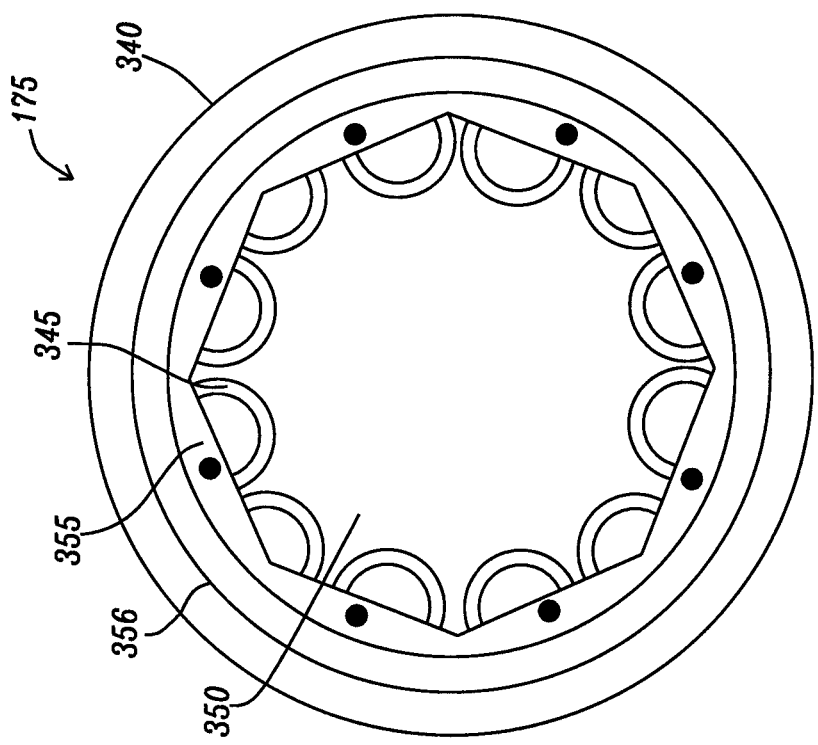

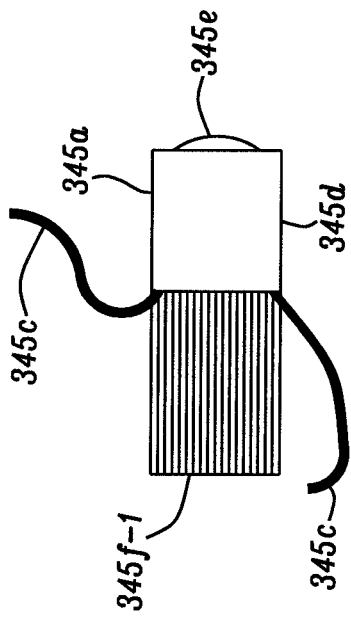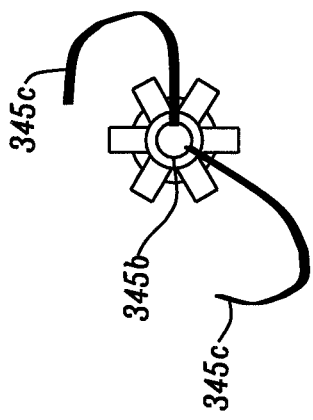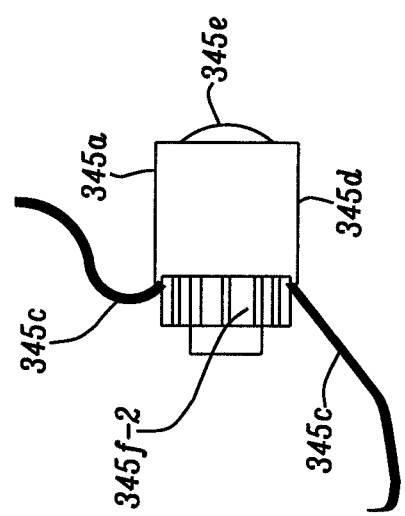

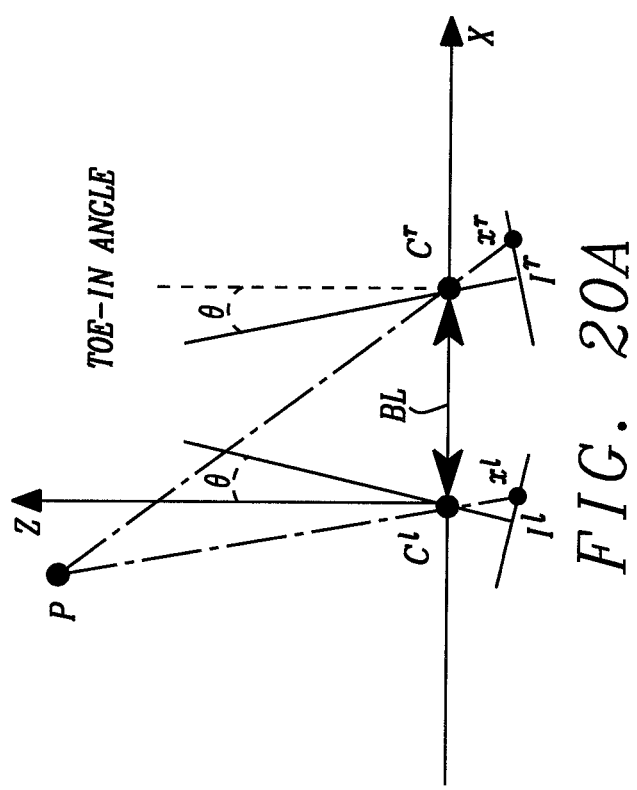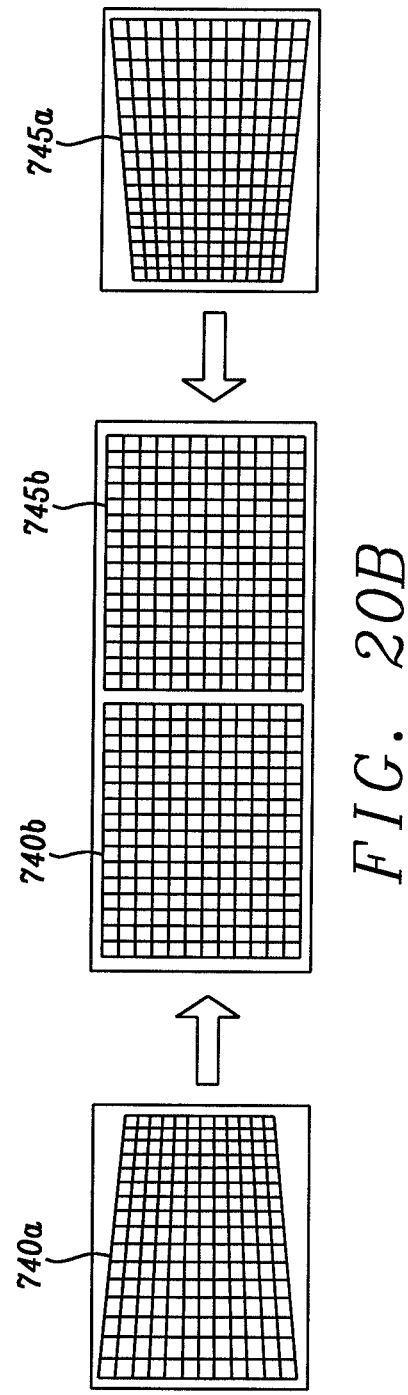

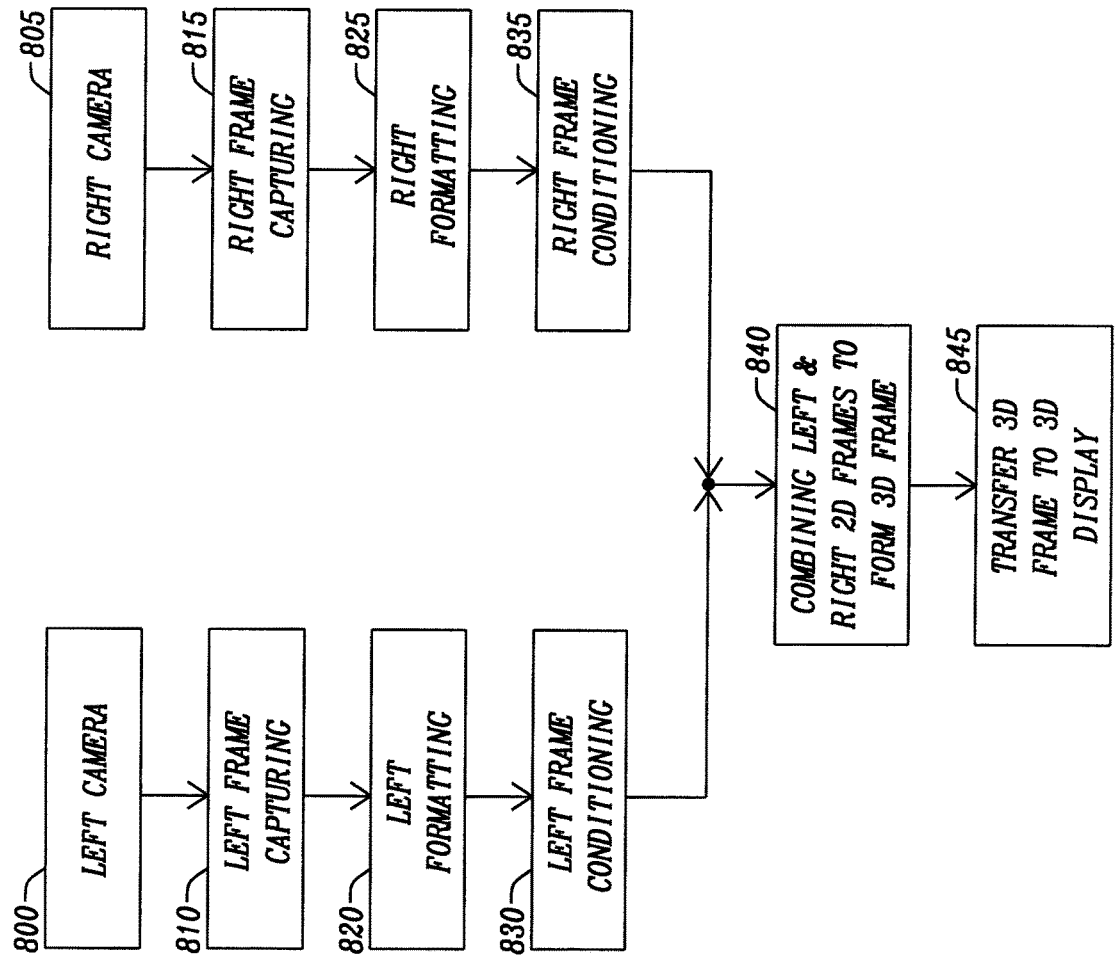

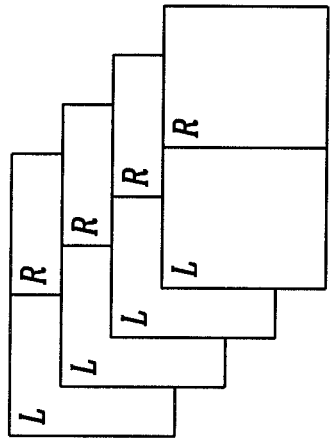
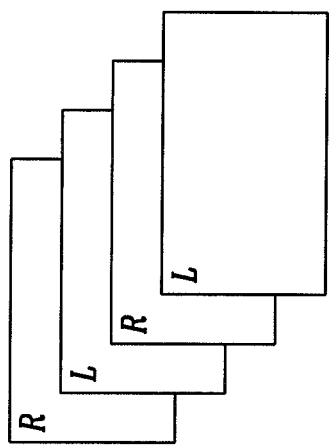
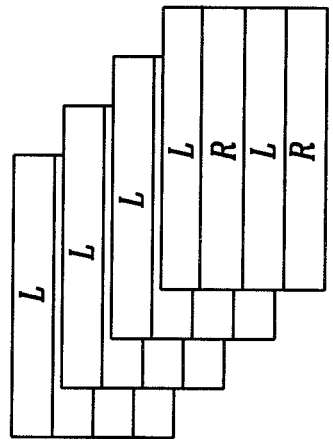
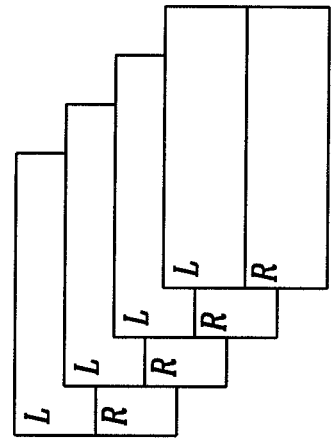

| STAGE →<br>TIMELINE ↓ | I/O INTERFACE 515<br>CAPTURING | 505a<br>CORE 1<br>FORMATTING | 505b<br>CORE 2<br>CONDITIONING | 505c<br>CORE 3<br>3D COMBINATION | 515<br>I/O INTERFACE<br>3D DISPLAY |
|---|---|---|---|---|---|
| 1st TIME SLOT | 1st FRAME PAIR | N/A | N/A | N/A | N/A |
| 2nd TIME SLOT | 2nd FRAME PAIR | 1st FRAME PAIR | N/A | N/A | N/A |
| 3rd TIME SLOT | 3rd FRAME PAIR | 2nd FRAME PAIR | 1st FRAME PAIR | N/A | N/A |
| 4th TIME SLOT | 4th FRAME PAIR | 3rd FRAME PAIR | 2nd FRAME PAIR | 1st FRAME PAIR | N/A |
| 5th TIME SLOT | 5th FRAME PAIR | 4th FRAME PAIR | 3rd FRAME PAIR | 2nd FRAME PAIR | 1st FRAME PAIR |
| 6th TIME SLOT | 6th FRAME PAIR | 5th FRAME PAIR | 4th FRAME PAIR | 3rd FRAME PAIR | 2nd FRAME PAIR |
| nth TIME SLOT | nth+4 FRAME PAIR | nth+3 FRAME PAIR | nth+2 FRAME PAIR | nth+1 FRAME PAIR | nth FRAME PAIR |

MICROSCOPE MADE WITH CMOS CAMERA(S)

The present invention is a divisional application that claims priority under 35 U.S.C. § 120 from U.S. patent application Ser. No. 16/505,951, filing date Jul. 9, 2019, now U.S. Pat. No. 11,340,441, issued May 24, 2022, which is assigned to a common assignee and incorporated herein by reference in its entirety.

TECHNICAL FIELD

This disclosure relates generally to medical microscopes, particularly to a medical three dimensional (3D) microscope. Even more particularly, this disclosure relates to a medical microscope with light emitting diode (LED) illumination with focus and intensity control. Still more particularly, this disclosure relates to a medical 3D microscope with an image processor that generates 3D images from two dimensional (2D) images.

BACKGROUND 3D images and devices have been broadly applied in many fields, including medical surgery and examination. In a surgical application of a 3D microscope, there should be virtually no lag between a surgical action such as a surgeon manipulating a surgical sample within the view of the microscope and what appears on the screen. The typical latency is approximately 60 msec. This latency period in developing the 3D will cause a perceptible lag.

In current implementations of a 3D microscope, the "depth of field" or depth of view is less 1 mm.

"Computational Imaging for 3D Micrographs with 10-Fold Depth-of-Field Enhancement" Carles, et al SPIE Newsroom, Mar. 7, 2017, DOI: 10.1117/2.1201611.006749 found Apr. 2, 2019, at http://spie.org/newsroom/6749-computational-imaging-for-3d-micrographs-with-10-fold-depth-of-field-enhancement, states that focus today depends on engineering optical elements to optimally focus light from the sample to form a sharp image at a single plane. A specific sample plane is inherently defined so that objects not located exactly in the sample plane are out of focus. In current implementations of a 3D microscope, the "depth of field" or depth of view is less 1 mm. In high-resolution microscopy, the depth of field (DOF) over which a sharp image is recorded is typically a 1 μm or less, which offers the benefit of optical sectioning (i.e., the ability to produce clear images of focal planes within a thick sample). However, samples that exceed the DOF of a microscope are the norm, which means it is necessary to refocus the image throughout its depth to build a clear picture.

One solution to this problem was to record a single image as the sample was swept through the plane of best focus. A coherent optical processor is used to recover a sharp image. A more modern approach records a 'Z-stack' of up to 100 images and computationally combines the images into a single sharp image with an extended depth of field. Other techniques have been developed for high-resolution 3D microscopes, such as light-sheet fluorescence microscopy, confocal/multiphoton microscopy, and localization super-resolution microscopy (although the latter two are not strictly 3D techniques in themselves). Due to their scanning nature, however, none of these techniques can be used for a snapshot or video-rate imaging.

SUMMARY

An object of this disclosure is to provide a medical/surgical microscope configured for real-time video display with the function of recording and broadcasting simultaneously during surgery.

Another object of this disclosure is to provide a medical/surgical microscope with sufficiently small latency to have an image displayed on a monitor with imperceptibly small latency.

Further another object of this disclosure is to provide a medical/surgical microscope with a depth of field of approximately 4 mm.

Still further, another object of this disclosure is to provide a medical/surgical microscope with two or more cameras configured for capturing two or more images of specimens being observed by the microscope.

Even further, another object of this disclosure is to provide a medical/surgical microscope with a computer system that has a non-transitory memory apparatus for storing computer program code configured for digitally rendering real-world medical/surgical images.

Even still further, another object of this disclosure is to provide a medical/surgical microscope with an illumination system that has controls for focusing and regulating lighting of a specimen being observed Even still further, another object of this disclosure is to provide a medical/surgical microscope with a control system configured for adjusting the toe-in angle of two cameras and for adjusting a convergence point in the 3D microscope.

To accomplish at least one of these objects, a 3D microscope system includes two or more digital cameras configured for capturing medical/surgical specimen object images. The two or more digital cameras are each coupled to one of the two or more lenses configured for magnifying an image of a medical/surgical specimen object. The two or more digital cameras are attached to two or more camera mounts. Each of the two or more camera mounts can be rotated such that each of the two or more cameras and lenses have a toe-in angle such that each of the two or more cameras and lenses are pointed at a common point of the medical/surgical specimen object.

In various embodiments, the 3D microscope system is equipped with an illumination apparatus. The illumination apparatus has a plurality of LED lamps mounted to a ring and configured with an illumination control system to manipulate the light from the LED lamps to control focus and illumination of the light upon the medical specimen.

In some embodiments, each of the two or more camera mounts are affixed to one rotary table of two or more rotary tables. The two or more rotary tables are rotated such that each of the two or more cameras and lenses are situated such that each of the two or more cameras and lenses are pointed at a common point of the medical/surgical specimen object.

In various embodiments, each of the two or more camera mounts are affixed to a camera platform. In other embodiments, each of the two or more rotary tables are affixed to the camera platform. The camera platform is connected to a z-axis lead block of a z-axis leadscrew assembly. The z-axis leadscrew assembly has a threaded leadscrew that is connected to a z-axis motor that adjusts the z-axis lead block and thus the camera platform with the two or more cameras and lenses to along the z-axis.

The camera platform is connected to a z-axis lead screw block of a z-axis leadscrew assembly. The z-axis leadscrew assembly has a threaded z-axis leadscrew that is connected to a z-axis motor that adjusts the z-axis lead block and thus the camera platform with the two or more cameras and lenses to along the z-axis. A z-axis leadscrew block has a threaded, circular opening such that the leadscrew block is threaded onto the leadscrew. The z-axis leadscrew block is coupled to the camera so that when the z-axis leadscrew is rotated, the camera moves in the axis of the z-axis leadscrew. A first bearing is placed at one end of the z-axis leadscrew and secured to permit rotation of the leadscrew. A second bearing placed is at a second end of the leadscrew and secured to permit rotation of the leadscrew. A z-axis motor is coupled to the second bearing and secured such that when the z-axis motor receives power the z-axis lead screw is rotated to adjust the camera with the camera along the axis of the leadscrew.

In various embodiments, an angle leadscrew assembly is attached to the camera platform for adjusting the angle of each of the two or more camera mounts and thus a toe-in angle of the two or more cameras such that the two or more cameras are directed to a common point on the medical/surgical specimen. The angle leadscrew assembly has an angle adjustment leadscrew that has a threaded, circular opening such that a spring lead block assembly is threaded onto the angle adjustment leadscrew. The spring lead block assembly has a routed opening into which a spring is secured. A third bearing is placed at one end of the angle adjustment leadscrew and secured to the camera to permit rotation of the angle adjustment leadscrew. A fourth bearing is placed at a second end of the angle adjustment leadscrew and secured to the camera to permit rotation of the angle adjustment leadscrew. An angle adjustment motor is coupled to the fourth bearing and secured such that when the z-axis motor receives power the z-axis lead screw is rotated to adjust the angle of the camera mount to adjust the toe-in of the one or more cameras.

Each camera mount is affixed to one of the two or more rotary tables. Each of the two or more camera mounts has an open slit-leg that is coupled to the spring attached to the spring lead block assembly. The spring lead block assembly is threaded onto the angle adjustment leadscrew to affix one of the two or more camera mounts to one of the two or more angle adjustment leadscrews. The two or more angle adjustment leadscrews are each connected to an angle adjustment leadscrew adjustment motor of two or more angle adjustment leadscrew adjustment motors that each adjusts the angle of each of the two or more cameras and lenses, independently.

A motor controller is connected to the z-axis motor and the leadscrew angle adjustment motor for providing control signals to adjust the focus and convergence of the two or more cameras.

In various embodiments, the camera platform is movably secured to an equipment stand that is stabilized to permit the 3D microscope system to be sufficiently close to an examined specimen. The z-axis leadscrew motor and the z-axis leadscrew are affixed to the equipment stand such that the z-axis leadscrew motor can turn the z-axis leadscrew to move the camera mounting platform and the two or more cameras and lenses to along the axis of the z-axis lead screw and parallel to a long axis of the equipment stand.

In other embodiments, the camera mounting platform is affixed to a moveable arm of a medical cart. The camera mounting platform is surrounded by a camera module cover. Integrated within the module cover, in close proximity to the camera mounting platform, is the illumination apparatus. The movable arm of the 3D microscope system can be moved to view medical specimens at any angle.

The microscope system has an image processor that receives a two-dimensional (2D) image data stream from each of the two or more digital cameras. The image processor comprises multiple processor cores, where each processor core has multiple floating point processing units and multiple integer processing units. The image processor further includes a non-transitory memory device that is readable by the multiple processor cores. The non-transitory memory device has a program of instructions stored on it that is executable by the multiple processor cores to perform a method for converting 2D images microscopic images into 3D microscopic images for display on a 3D monitor included as part of the 3D microscope system.

The method begins with organizing the multiple floating point processing cores and the multiple integer processing cores multiple parallel pipelines for processing the 2D images. The 2D images are captured by the two or more digital cameras in a plurality of sequential frames that are transferred to the image processor. Each of the frames is formatted to resize or convert the two or more 2D images captured by the two or more digital cameras to a conforming format for the 3D monitor. The two or more formatted images are then conditioned to calibrate, rectify, and equalize the color/brightness to better match the two or more frames. The rectification corrects any image distortion among the two or more cameras. The resolution and equalization align any color/brightness difference among the two or more cameras. The two or more 2D images are then combined to form the 3D image which is then displayed.

The parallel pipelines of the multiple processor cores permit multiple frames of the two or more 2D images to be processed simultaneously to allow the 3D image to be displayed in a real-time sequence with a latency of approximately 10 to 20 msec.

BRIEF DESCRIPTION OF THE DRAWINGS

FIGS. 2A-2C are diagrams of a camera and lens of the 3D microscope system of FIG. 1 embodying the principles of the present disclosure.

FIGS. 5A and 5B are diagrams respectively of the front and side view of a camera mount of the 3D microscope system of FIG. 1 embodying the principles of the present disclosure.

FIGS. 6A and 6B are diagrams respectively of the front and side view of a rotary table of the 3D microscope system of FIG. 1 embodying the principles of the present disclosure.

FIGS. 9A-9D are diagrams of component parts of a 3D microscope of FIG. 8 embodying the principles of the present disclosure.

FIG. 12A is a diagram of a top view and FIG. 12B is a diagram of a bottom view of an LED illumination apparatus within a 3D microscope system embodying the principles of the present disclosure.

FIGS. 13A, 13B, and 13C are diagrams of an LED lamp used in the LED illumination apparatus of FIGS. 12A and 12B embodying the principles of the present disclosure.

FIG. 20A is a graph of the geometry for the causes of the keystone distortion due to toe-in of the cameras of the 3D microscope system embodying the principles of the present disclosure.

FIG. 20B is a graph of the rectification of keystone distortion due to toe-in of the cameras of the 3D microscope system embodying the principles of the present disclosure.

FIG. 21 is a flow chart of a method for converting 2D images microscope images into 3D microscope images for display on a 3D monitor included as part of the 3D microscope system embodying the principles of the present disclosure.

FIGS. 22A-22E are diagrams of the video monitor frame formats after combining the cameras video images of the 3D microscope system embodying the principles of the present disclosure.

FIG. 23 is a diagram of a parallel pipeline structure of the multi-core image processor performing the method for converting 2D images microscopic images into 3D microscopic images for display on a 3D monitor included as part of the 3D microscope system embodying the principles of the present disclosure.

DETAILED DESCRIPTION

A medical/surgical 3D microscope system is configured for a low latency real-time video display with a relatively large depth of field. The medical/surgical 3D microscope system is configured with the function of recording and broadcasting simultaneously during surgery. The medical/surgical 3D microscope system has two or more cameras configured for capturing two or more images of specimens being observed by the microscope. Each of the two or more cameras is connected to a high definition, ultra-low distortion lens. The medical/surgical 3D microscope system has an image processing computer system having a non-transitory memory apparatus for storing a computer program code configured for digitally rendering real-world medical/surgical images. The medical/surgical 3D microscope includes an illumination system with controls for focusing and regulating lighting of a specimen being observed. The medical/surgical 3D microscope has a control system for activating motors for adjusting the toe-in angle of the two or more cameras and for adjusting a convergence point in the 3D microscope. The medical/surgical 3D microscope has a display configured for displaying 3D images when viewed with 3D glasses or goggles.

Figure 1:
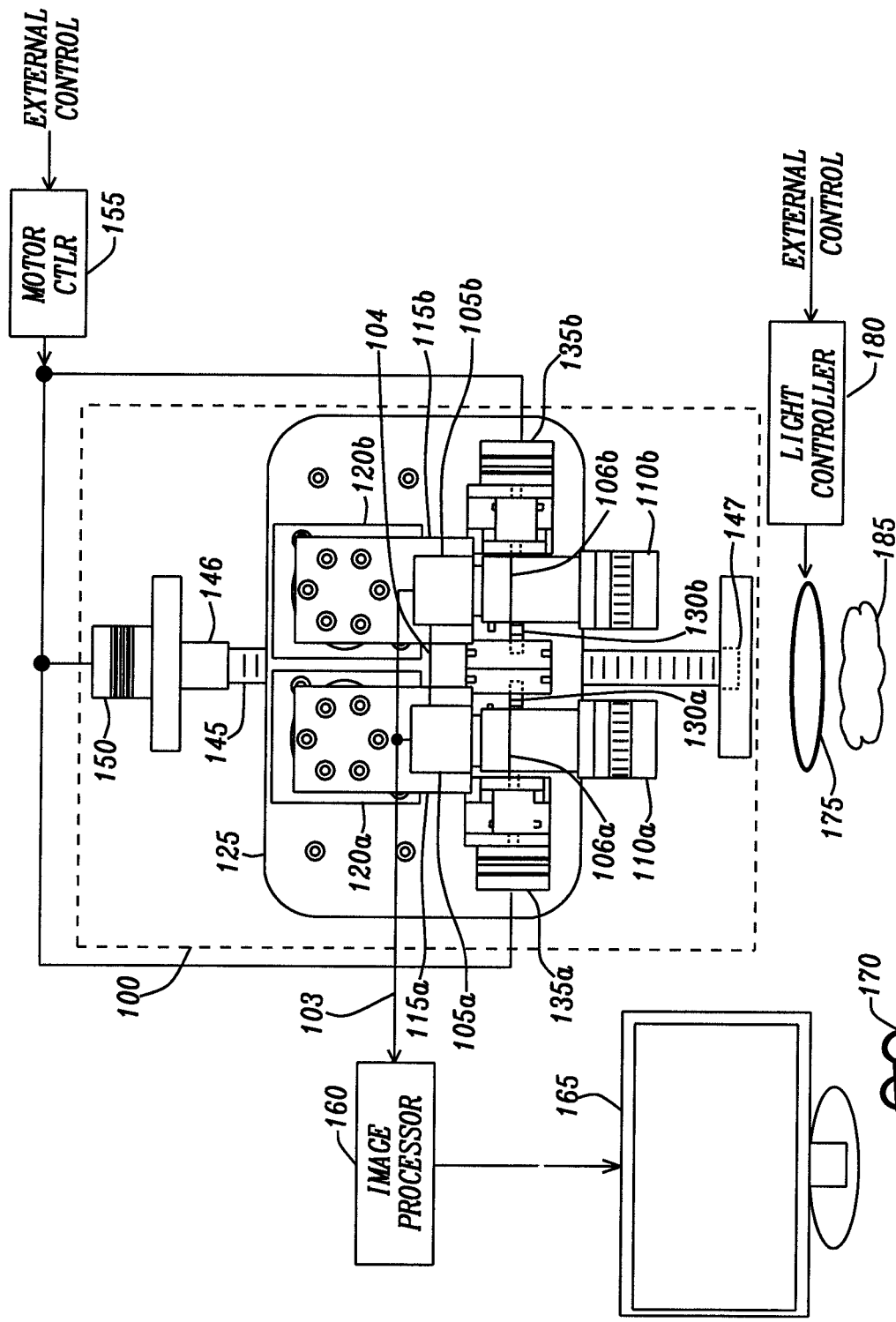
FIG. 1 is a structural diagram of a 3D microscope system embodying the principles of the present disclosure.

FIG. 1 is a structural diagram of a first implementation of a 3D microscope system embodying the principles of the present disclosure. The 3D microscope system has a 3D microscope 100 for capturing two 2D images of a specimen 185. The 3D microscope has two digital cameras 105a and 105b connected to two lenses 110a and 110b. The two lenses 110a and 110b have a high resolution for providing high definition. An example of the two lenses 110a and 110b is a Computar M5028 lens from CBC Co., Ltd., Tokyo, Japan. The two digital cameras 105a and 105b are commercially available cameras that meet or exceed the current requirements for the medical/surgical environment of 60 fps and 1920×1080 resolution. An example of the two cameras 105a and 105b is a Flir Blackfly USB3 camera sensor from FLIR Integrated Imaging Solutions Inc., Richmond, BC, Canada.

The two digital cameras 105a and 105b are coupled to the two lenses 110a and 110b by two lens holders 106a and 106b. Each of the cameras 105a and 105b is affixed to one of the two camera mounts 115a and 115b. Each of the two camera mounts 115a and 115b is in turn coupled to one of the two rotary tables 120a and 120b. The two rotary tables 120a and 120b are rotated such that each of the two camera mounts 115a and 115b and therefore each of the two digital cameras 105a and 105b and the two lenses 110a and 110b are pointed at a common point of the medical/surgical specimen 185.

The two rotary tables 120a and 120b are secured to a mounting platform 125 through a rotating table bearing 121 (described hereinafter) that allows the two rotary tables 120a and 120b and thus the two digital cameras 105a and 105b and the two lenses 110a and 110b to be rotated. Each of the two camera mounts 115a and 115b is coupled to one of the two camera mount leadscrews 130a and 130b through a spring lead block and an open slit-leg (shown and discussed hereinafter). The two camera mount leadscrews 130a and 130b are each connected to a camera mount adjustment motor 135a and 135b that each adjusts the angle of each of the two cameras 105a and 105b and lenses 110a and 110b, independently.

A motor controller 155 is connected to the z-axis motor 150 and the rotary table adjustment motors 135a and 135b to provide control signals to adjust the height and convergence of the two cameras 105a and 105b and lenses 110a and 110b for improving the 3D image on the monitor.

The z-axis motor 150 is connected to the z-axis leadscrew 145 through a top z-axis bearing 146. The top z-axis bearing 146 and a bottom z-axis bearing 147 are secured to a stationary stand described hereinafter. The top z-axis bearing 146 and a bottom z-axis bearing 147 allow the z-axis leadscrew 145 to be turned freely by the z-axis motor 150. A z-axis lead block (described hereinafter) is threaded onto the z-axis leadscrew 145 and fastened to the mounting platform 125 to adjust the height of the cameras 105a and 105b and lenses 110a and 110b for adjusting the 3D effect on the monitor.

Each of the two cameras 105a and 105b have an output port that is connected with a Universal Serial Bus 3 (USB-3) cable 103 to the image processor 160 to receive the digital video frame data from the two cameras 105a and 105b. The image processor 160 may be any multicore computer processor capable of handling multiple parallel pipeline operations to convert the two digital video frame data streams from the two cameras 105a and 105b to a 3D image. The data for the 3D image may comply with, for example, a High-Definition Multimedia Interface (HDMI), VESA DisplayPort, or a Digital Visual Interface (DVI). The image processor 160 is connected with a monitor 165 that is capable of displaying either 2D and/or 3D images. The 3D image data is transferred from the image processor 160 to the monitor 165 for display. In displaying the 3D image, the observer may need a pair of polarized glasses 170 to allow the observer to experience the 3D effect.

The two cameras 105a and 105b are connected together with a general purpose input/output (GPIO) cable 104 to provide a synchronized capture signal from the camera 105a or 105b to a secondary camera 105b or 105a. Synchronized capture is when one "primary" camera 105a or 105b is used to trigger the "secondary" camera 105b or 105a, using the primary camera's strobe. The synchronized capture ensures that the frame rate of the secondary camera 105b or 105a is the same as that of the primary camera 105a or 105b. Strobes occur when cameras 105a and 105b begin to capture images. The GPIO connection on the cameras 105a or 105b uses the strobe output as an input for other cameras 105b or 105a.

Placed between the two cameras 105a and 105b and lenses 110a and 110b and the medical/surgical specimen 185 is an illumination apparatus 175. The illumination apparatus has a plurality of LED lamps mounted to a ring and configured with a light controller 180 to manipulate the light from the LED lamps to control focus and illumination of the light upon the medical/surgical specimen 185. The illumination apparatus 175 is described in greater detail hereinafter.

FIGS. 2A-2C are diagrams of a camera 105 and lens 110 of the 3D microscope system 100 of FIG. 1 embodying the principles of the present disclosure. In FIG. 2A, the camera 105 is shown with an enclosure 195 having two connectors 196 and 197 and a light emitting diode (LED) status indicator 198 at the rear surface. The first connector 196 is a USB3 connector into which the USB3 cable 103 is connected. The USB3 connection transfers the image data from the camera 105 to the image processor 160 of FIG. 1. for conversion from the two 2D images to a 3D image. The second connector 197 is a GPIO connector that connects the two cameras to allow the transfer of strobe signals for synchronized capture between two of the cameras 105.

Further in FIG. 2A, the case of the camera 195 has a lens holder 106 fabricated to be integral with the case. The lens 110 has a mating lens mount that mates with the lens holder 106 to secure the lens 110 in place. The lens 110 is structured to provide the magnification suitable for performing medical and surgical procedures. FIG. 2B shows the case 195 of the camera 105 with the lens holder 106 attached. The top surface of the case 195 as shown in FIG. 2B has fastener receptacles 199 set in the case 195 for receiving bolts, screws, or studs for securing the camera 105 to the camera mount 115a and 115b of FIG. 1.

Referring now to FIG. 2C, the camera 105 has a sensor module 108 that receives light through the lens 100 for detecting an image. The sensor module includes a first printed circuit board 108a having a CMOS image sensor 108b mounted on it. The CMOS image sensor 108b is formed of an array of active pixel sensors that are fabricated using processes that are consistent with a complementary metal oxide semiconductor (CMOS) processes. The active pixel sensor is a light sensing device with sensing circuitry inside each pixel. Each active pixel sensor includes a sensing element formed in a semiconductor substrate and capable of converting photons of light into electronic signals. As the photons of light strike the surface of a photoactive region of the solid-state image sensors, free charge carriers are generated and collected. Once collected, the charge carriers often referred to as charge packets or photoelectrons are transferred to output circuitry for processing.

An active pixel sensor also includes one or more active transistors within the pixel itself. The active transistors amplify and buffer the signals generated by the light sensing element to convert the photoelectron to an electronic signal prior to transferring the signal to a common conductor that conducts the signals to an output node. The output signals are transferred from the first printed circuit board 108a to a second printed circuit board 108c. The second printed circuit board 108c includes processing circuitry that receives the electronic image signals from the CMOS image sensor 108c and converts it to digital signals that are encoded to the appropriate image format such as High-Definition Multimedia Interface (HDMI), VESA DisplayPort, or a Digital Visual Interface (DVI). The output of the second printed circuit board 108c is connected to the connectors 105b for transfer to the associated camera 105a or 105b for synchronization of two cameras 105a and 105b for transfer to the image processor 160 for further processing.

Figure 3:
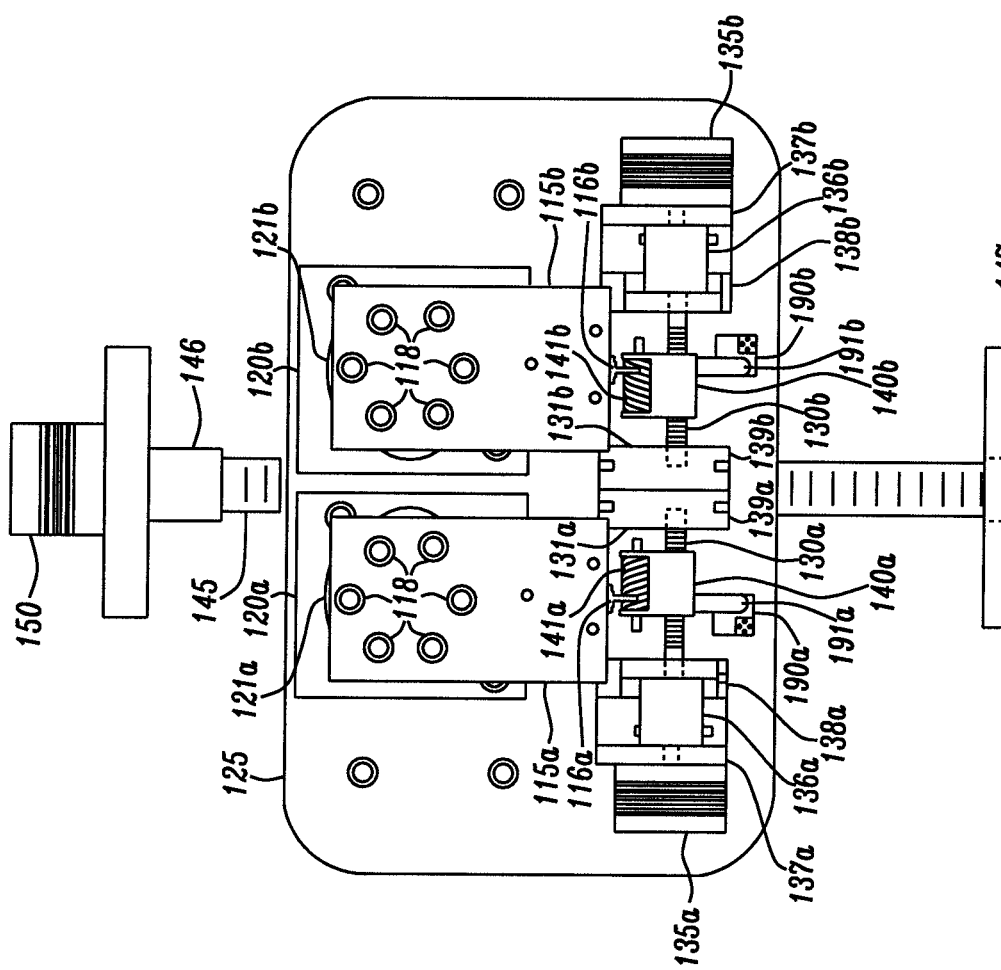
FIG. 3 is a diagram of the 3D microscope of FIG. 1 showing details of the camera adjustment mechanism embodying the principles of the present disclosure.

FIG. 3 is a diagram of the 3D microscope of FIG. 1 showing details of the camera adjustment mechanism embodying the principles of the present disclosure. FIG. 3 is the 3D microscope 100 of FIG. 1 with the cameras 105a and 105b and lenses 110a and 110b removed. The camera mounts 115a and 115b have fastener openings 118 that are aligned with openings formed in the rotary table bearing 121a and 121b. The rotary table bearings 121a and 121b are seated in the rotary table bases 120a and 120b to allow free rotation of the rotary table bearings 121a and 121b and discussed further hereinafter. The rotary table bases 120a and 120b are secured to the camera platform 125.

The open slit-legs 116a and 116b couple the camera mounts 115a and 115b into the coils of the springs 141a and 141b to couple the camera mounts 115a and 115b to spring lead blocks 140a and 140b. The spring lead blocks 140a and 140b are threaded to the camera mount adjustment leadscrews 130a or 130b. The two camera mount leadscrews 130a and 130b are each connected through the bearings 136a and 136b to camera mount adjustment motors 135a and 135b. The bearings 136a and 136b and the camera mount adjustment motors 135a and 135b are fastened to the brackets 137a, 137b, 138a, 138b, 139a, and 139b. The brackets 137a, 137b, 138a, 138b, 139a, and 139b are attached to the camera platform 125 for securing the bearings 136a and 136b and the camera mount adjustment motors 135a and 135b and thus the camera mount adjustment leadscrews 130a or 130b.

The open slit-legs 116a and 116b are set into the springs 141a and 141b to allow an angle of the camera mounts 115a and 115b to be adjusted such that the focal point of the lenses 110a and 110b can be adjusted to meet the required toe-in to have proper convergence on the medical/surgical specimen 185. The open slit-legs 116a and 116b as placed into the coils of the springs 141a and 141b allow the camera mounts 115a and 115b and thus the two digital cameras 105a and 105b and the two lenses 110a and 110b to be rotated by a fixed amount. To prevent binding of the camera mounts 115a and 115b and the spring lead blocks 140a and 140b, a binding sensors 190a and 190b and a sensor blades 191a and 191b are incorporated to sense the location of the spring lead blocks 140a and 140b relative to the position where binding occurs. The sensor blades 191a and 191b are each connected to one of the spring lead blocks 140a and 140b and each sensor blade 191a and 191b passes over an optical sensor to determine the location of each spring lead block 140a and 140b. The optical sensor is in communication with the motor controller 155 of FIG. 1. The motor controller 155 issues a stop command to the camera mount adjustment motors 135a and 135b to adjust the angle of the camera mounts 115a and 115b and thus the two digital cameras 105a and 105b and the two lenses 110a and 110b to the proper angle.

Figure 4:
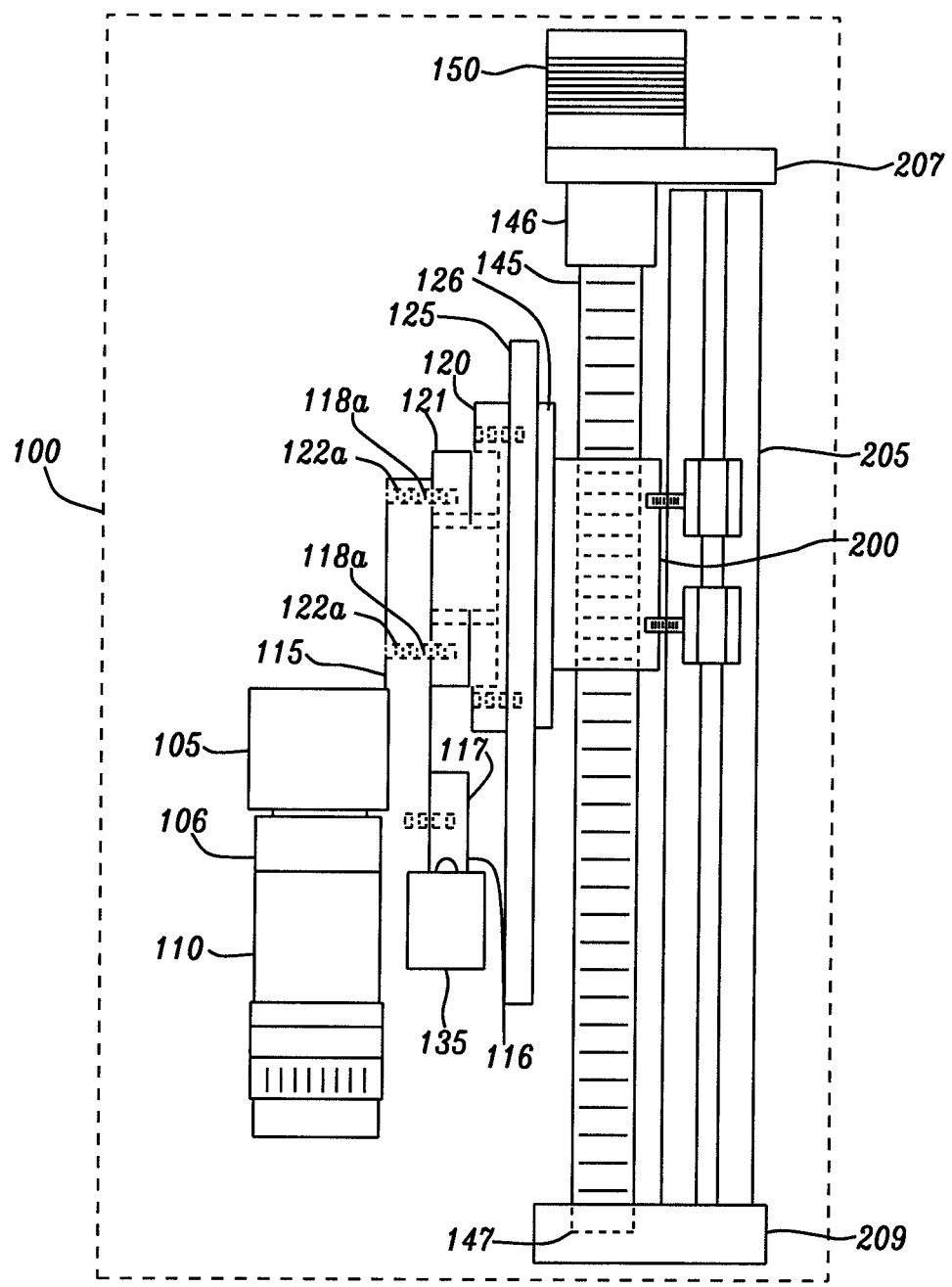
FIG. 4 is a diagram of a side view of the 3D microscope embodying the principles of the present disclosure.

FIG. 4 is a diagram of a side view of the 3D microscope system 100 embodying the principles of the present disclosure. The 3D microscope system 100 has a camera 105 with the lens 110 connected through the lens holder 106. The camera 105 is connected to the camera mount 115 with the fasteners 121 into the opening 118 of the rotary table bearing 121. The rotary table bearing 121 is seated in the rotary table base 120. The rotary table base 120 is then connected to the camera platform 125. The camera platform 125 has a spacer platform 126 that is connected to the z-axis lead block 200 to the camera platform 125. The z-axis lead block 200 is threaded to the z-axis leadscrew 145. As described above, the leadscrew 145 is connected to the bearings 146 and 147 to allow the leadscrew 145 free rotation when the z-axis motor 150 is activated for adjusting the height of the camera 105 with the lens 110 to adjust the 3D effect on the monitor 165.

The microscope system frame 205 has a top plate 207 that supports the z-axis motor 150 and the bearing 146. A bottom plate 209 is attached to the microscope system frame 205 and retains the bearing 147.

FIGS. 5A and 5B are diagrams respectively of the front and side view of a camera mount 115a or 115b of the 3D microscope system of FIG. 1 embodying the principles of the present disclosure. Referring to FIG. 5A, the camera mount has the fasteners 118a placed in the openings 118b in the camera mount 115 as shown in FIG. 5B.

The open slit-leg 116 is secured or fabricated as part of the block 117a. The block 117a is attached to the camera mount 115 with fasteners placed in the openings 117b. The openings 119a allow the placement of fasteners to attach the camera 105 to the camera mount 115.

FIGS. 6A and 6B are diagrams respectively of the front and side views of rotary tables 120 and 121 of the 3D microscope system of FIG. 1 embodying the principles of the present disclosure. The rotary table is composed of the rotary table base 120 and the rotary table bearing 121. The rotary table bearing 121 is seated in an opening in the rotary table base 120 to allow the rotary table bearing 121 to rotate smoothly on the rotary table base 120. The rotary table bearing 121 has multiple openings 122 that match the pattern of the fasteners 118a and opening 118b of the camera mount 115 of FIGS. 5A and 5B. The bearing race 124 is formed in the center of the rotating table bearing 121 to permit the smooth operation of the table bearing 121. The table base has fasteners 123a placed in openings 123b for affixing the rotary table to the camera platform 125 as shown in FIG. 4.

Figure 7B:
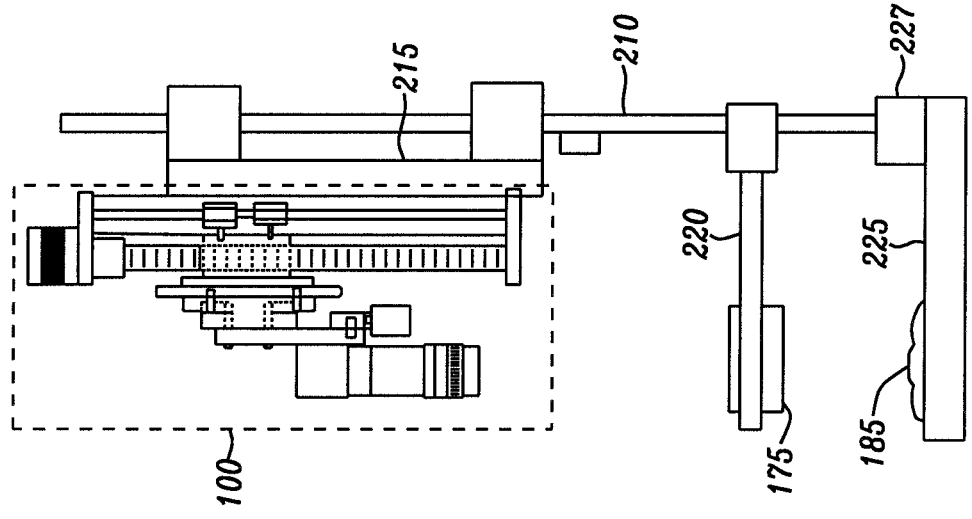
FIGS. 7A and 7B are diagrams respectively of the front and side view of the 3D microscope system of FIG. 1 with an equipment stand embodying the principles of the present disclosure.
Figure 7A:
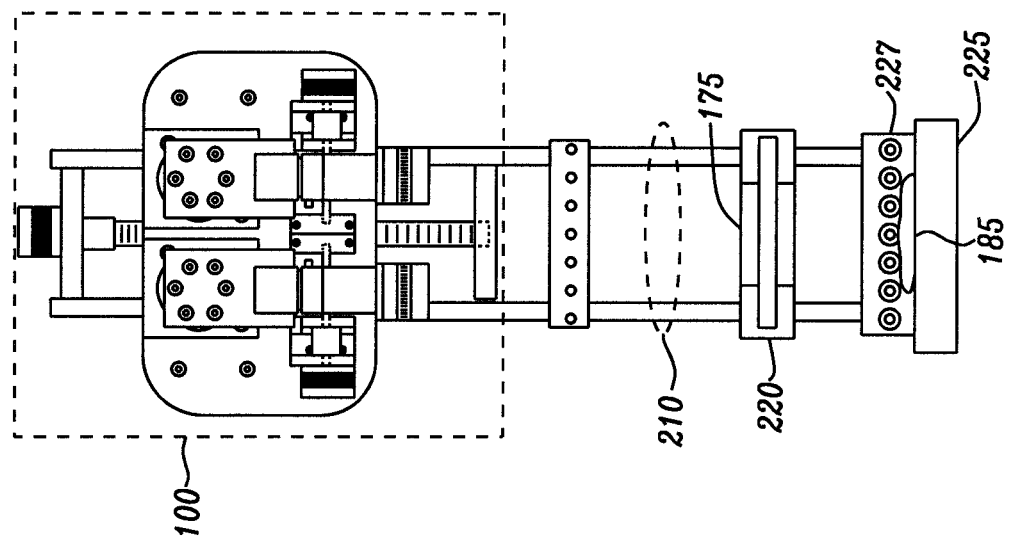

FIGS. 7A and 7B are diagrams respectively of the front and side view of the 3D microscope system 100 of FIG. 1 with an equipment stand embodying the principles of the present disclosure. The camera platform 125 onto which the 3D Microscope system 100 is mounted is, in turn, mounted to a support apparatus 215. The support apparatus 215 is secured to a pair of vertical rails 210 through openings in the support apparatus 215. The threaded fasteners are placed in the openings of the support apparatus 215 through each of the vertical rails 210 to securely fasten the microscope system 100 through the support apparatus 215 to the vertical rails 210 The vertical rails 210 may be cylindrical or rectangular in shape.

The illumination apparatus 175 is attached to a support arm 220 that is in turn connected to the vertical rails 210. A bottom stand 225 has a support block 227 that connects the vertical rails 210 to the stand 225. The medical/surgical specimen 185 may be placed on the bottom stand 225 for examination by the microscope system 100.

Figure 8:
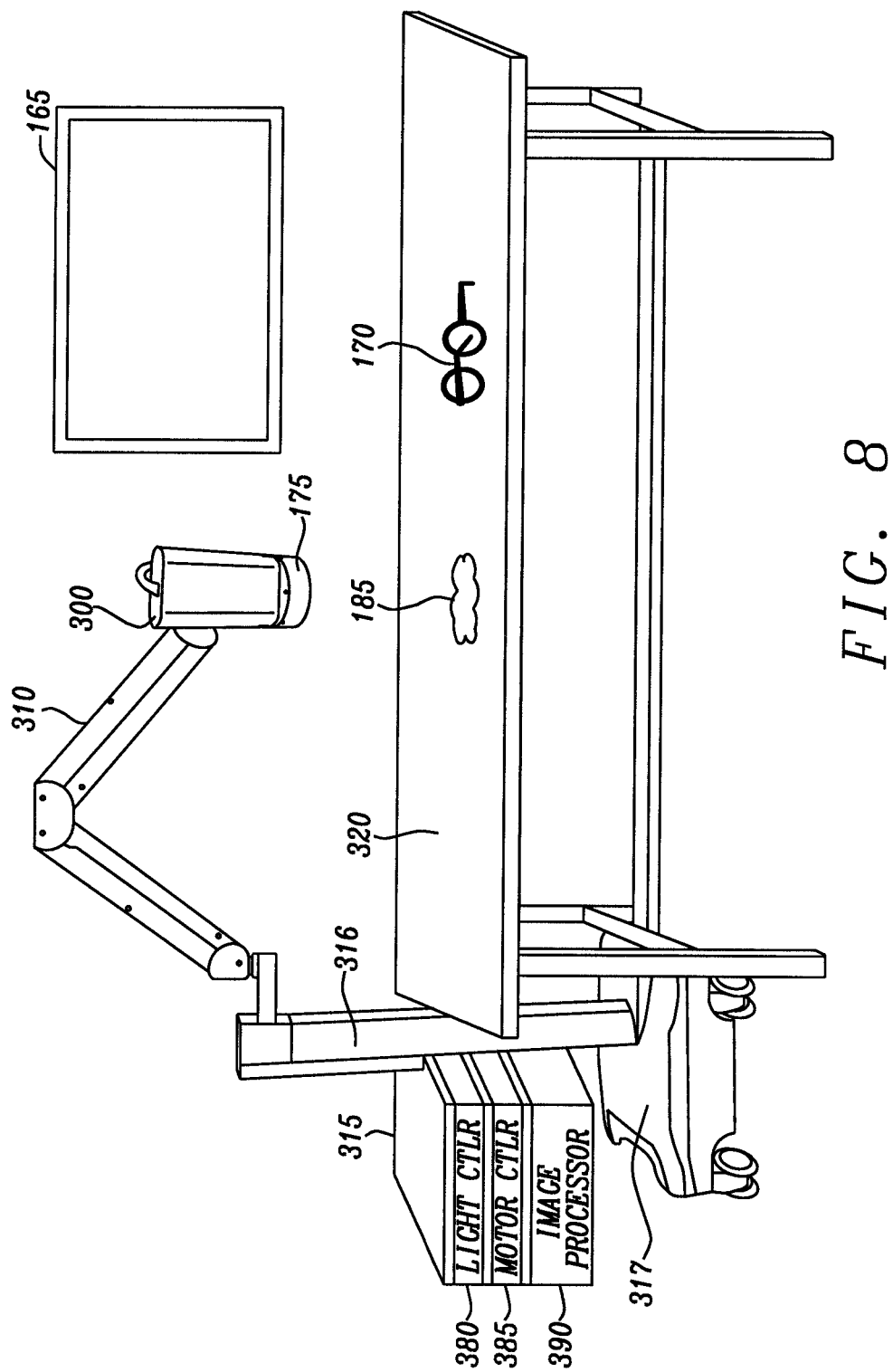
FIG. 8 is a diagram of an embodiment of a 3D microscope and medical equipment cart embodying the principles of the present disclosure.

FIG. 8 is a diagram of an embodiment of a 3D microscope 300 and medical equipment cart 315 embodying the principles of the present disclosure. The 3D microscope 300 has an illumination apparatus 305 connected to the enclosure of the 3D microscope 300. The 3D microscope 300 is connected to an articulated support boom 310 that is coupled to a vertical support column 316 of a medical equipment cart 315. The vertical support column 316 is attached to a medical equipment cart base 317. The medical cart base 317 is configured with wheels to permit the medical equipment cart 315 to be easily moved. The vertical support column 316 is configured to allow the attachment of shelving for holding the light controller 380, the motor controller 385, and the image processor 390.

The light controller 380 manipulates the light from the illumination apparatus 305 to control focus and illumination of the light upon the medical/surgical specimen 185. The motor controller 385 is connected to the 3D microscope 300 to provide control signals for adjusting the focus and convergence of the 3D microscope 300.

The image processor 390 receives the digital video frame data from the 3D camera 300. The image processor 390 may be any multicore computer processor capable of handling multiple parallel pipeline operations to convert the digital video frame data streams from the 3D microscope 300 to a 3D image. The data for the 3D image may comply with, for example, a High-Definition Multimedia Interface (HDMI), VESA Display Port, or a Digital Visual Interface (DVI). The image processor 390 is connected with a monitor 365 that is capable of displaying either 2D and/or 3D images. The 3D image data is transferred from the image processor 390 to the monitor 365 for display. In displaying the 3D image, the observer will need a pair of polarized glasses 170 to allow the observer to experience the 3D effect.

The medical equipment cart 315 abuts an operating table 320 The 3D microscope 300 is placed over the operating table 320 in close proximity to the medical/surgical specimen 185 for examination and performance of a medical or surgical procedure.

FIGS. 9A-9D are diagrams of component parts of a 3D microscope 300 of FIG. 8 embodying the principles of the present disclosure. FIG. 9A illustrates the closed case 300 with the enclosed 3D camera 300. The two USB cables 103a and 103b provide the digital video frame data from the 3D microscope 300. The illumination apparatus 175 at the lower portion of the 3D microscope 300 is configured providing sufficient light to illuminate the specimen 185. FIG. 9B shows the case 335 of the 3D microscope 300. The case 335 is formed of a material such as steel (stainless or carbon), aluminum, fiberglass, polycarbonate, polyamide, polystyrene, or other suitable organic polymers.

Referring now to FIG. 9C, the 3D microscope 300 has two digital cameras 105a and 105b connected to two lenses 110a and 110b. The two lenses 110a and 110b have high resolution for providing high definition as described in FIG. 1. The two digital cameras 105a and 105b that are coupled to the two lenses 110a and 110b by two lens holders 106a and 106b. Each of the cameras 105a and 105b is affixed to one of the two camera mounts 325a and 325b. Each of the two camera mounts 325a and 325b is in turn coupled to the mounting platform 360. The camera mounts 325a and 325b are permanently rotated such that each of the two digital cameras 105a and 105b and the two lenses 110a and 110b are pointed at a common point of the medical/surgical specimen 185.

The adjustment of the toe-in of the two digital cameras 105a and 105b and two lenses 110a and 110b are made by permanently adjusting the camera mounts 325a and 325b as described hereinafter. To ensure that the two digital cameras 105a and 105b and two lenses 110a and 110b are thoroughly secured, camera protection holders 330a and 330b hold the two lenses 110a and 110b in place at the correct angle when the 3D microscope 300 is moved with the articulated arm 310 of FIG. 8.

Each of the two cameras 105a and 105b has an output port that is connected with a Universal Serial Bus 3 (USB-3) cable 103a and 103b to the image processor 390 to receive the digital video frame data from the two cameras 105a and 105b. The two cameras 105a and 105b are connected together with a general purpose input/output (GPIO) cable 104 to provide a synchronized capture signal from the camera 105a or 105b to a secondary camera 105b or 105a. Synchronized capture is when one "primary" camera 105a or 105b is used to trigger the "secondary" camera 105b or 105a, using the primary camera's strobe. The Synchronized capture ensures that the frame rate of the secondary camera 105b or 105a is the same as that of the primary camera 105a or 105b. Strobes occur when one camera 105a and 105b begins to capture images. The GPIO connection 104 on the cameras 105a or 105b the use of the strobe output as an input for other cameras 105b or 105a.

FIG. 9D shows the component parts of the illumination apparatus 175. The case 340 is formed of the same materials as the case 335 of the 3D microscope 300 shown in FIG. 9B. A ring of LED lamps 345 is placed within the case 340. An opening 350 is placed in the upper surface of the case 340 to allow the cameras 105a and 105b and the lenses 110a and 110b to have a field of view through the illumination apparatus 175. The structure of the illumination apparatus 175 will be discussed hereinafter.

Figure 10:
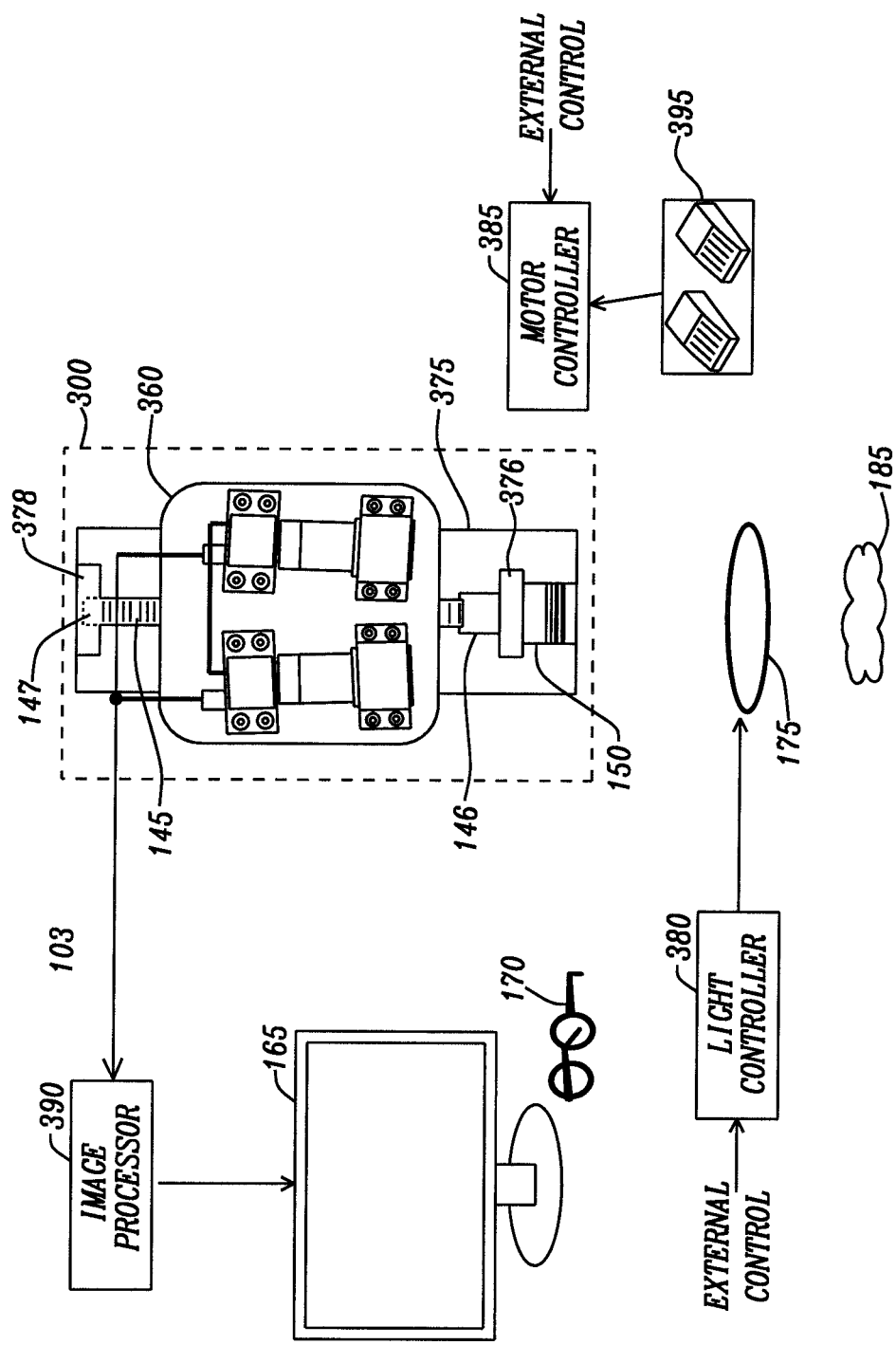
FIG. 10 is a structural diagram of a second example of a 3D microscope system embodying the principles of the present disclosure.

FIG. 10 is a structural diagram of a second example of a 3D microscope system embodying the principles of the present disclosure. The 3D microscope 300 is structured as described in FIG. 9C with the camera platform 360 being attached to a z-axis lead block (not visible) that is the same as the z-axis lead block 200 that is attached to the camera platform 125 as shown in FIG. 4. The z-axis motor 150 is attached to a lower end of the z-axis lead screw 145 through the bearing 146. The upper end of the leadscrew 145 is seated in the bearing 147 at the top of the z-axis lead screw 145.

The 3D microscope 300 has a microscope system frame 375 that has a bottom plate 376 that supports the z-axis motor 150 and the bearing 146. A top plate 378 is attached to the microscope system frame 375 and retains the bearing 147.

The motor controller 385 is connected to the z-axis motor 150 to provide control signals to adjust the focus of the two cameras 105a and 105b and lenses 110a and 110b. The top z-axis bearing 147 and a bottom z-axis bearing 146 allow the z-axis leadscrew 145 to be turned freely by the z-axis motor 150 for adjusting the height of the camera 105 with the lens 110 for adjusting the 3D effect. A z-axis lead block (not visible) is threaded onto the z-axis leadscrew 145 and fastened to the mounting platform 360 for adjusting the height of the cameras 105a and 105b and lenses 110a and 110b.

As described above, the image processor 390 receives the digital video frame data from the cameras 105a and 105b by way of the USB cables 103. The image processor 390 receives the two 2D image data streams and processes them into the 3D image frames that are transmitted to the display 165.

The light controller 380 receives external control signals that determine the intensity of the lighting created by the illumination apparatus 175. The illumination apparatus 175 will be described in greater detail hereinafter.

In addition to external controls, the motor controller 385 receives control signals from the footswitch 395. These signals determine the amount of movement along the z-axis the camera make in focusing the cameras 105a and 105b and lenses 110a and 110b.

Figure 11A:
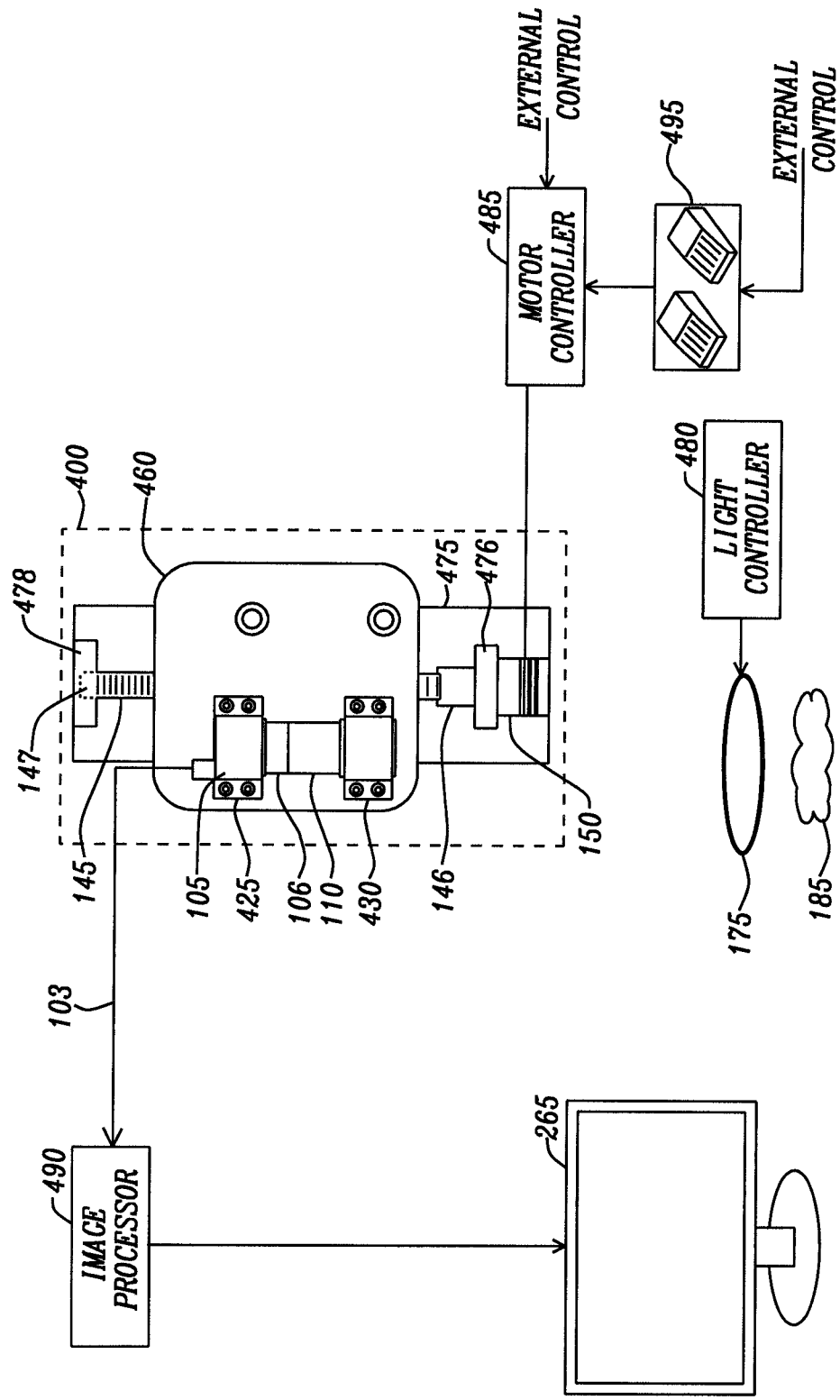
FIGS. 11A and 11B are structural diagrams of an example of a 2D microscope system with a single camera embodying the principles of the present disclosure.
Figure 11B:
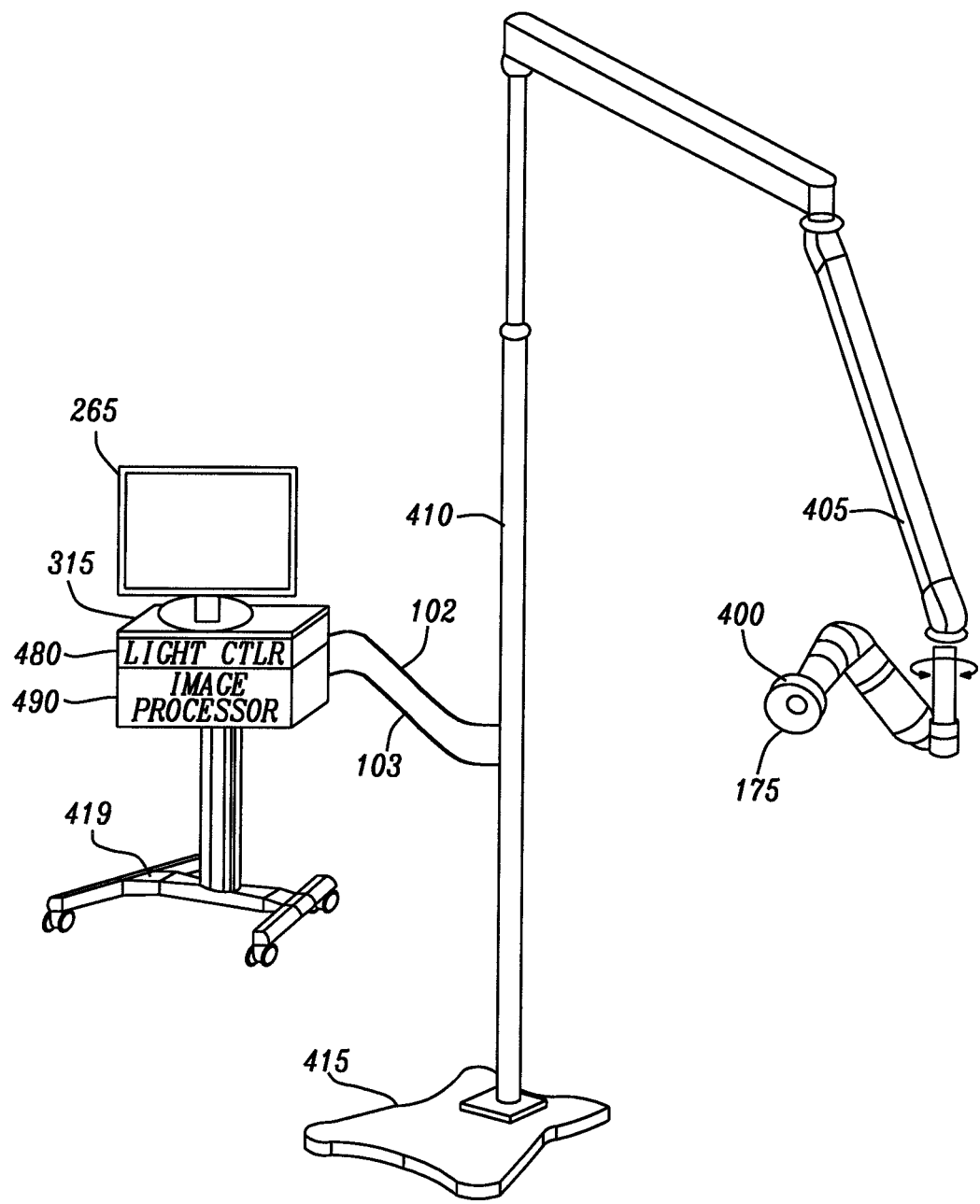

FIGS. 11A and 11B are structural diagrams of an example of a 2D microscope system embodying the principles of the present disclosure. The 2D microscope system has a 2D microscope 400 with a single camera 105 with a lens 110. The lens 110 is connected to the lens holder 106 and thus to the camera 105. The camera mount 425 is attached to the camera 105 and the camera protection holder 430 holds the lens 110 in place. The camera mount 425 and the camera protection holder 430 are fastened to the camera platform 460 to secure the camera 105 and the lens 110.

A USB cable 103 is plugged to a receptacle connector 196 of FIG. 2A. The USB cable 103 is connected to the image processor 490. A video stream is transmitted from the camera 105 through the USB cable 103 to the image processor 490. The image processor 490 conditions the video stream to the formatted video signal that is transferred to the display 165.

The camera platform 460 is connected to a spacer platform (not visible but similar to the spacer platform 126 of FIG. 4). The spacer platform is connected to a z-axis lead block (not visible) to connect the camera platform 460 to the z-axis lead block. The z-axis lead block is also not visible but is identical to the z-axis lead block 200 of FIG. 4.

The z-axis lead block is threaded to the z-axis leadscrew 145. As described above, the leadscrew 145 is connected to the bearings 146 and 147 to allow the leadscrew 145 free rotation when the z-axis motor 150 is activated for adjusting the height of the camera 105 with the lens 110. The z-axis motor 150 is connected to the bearing 146 through the bottom plate 476. The bearing 147 is seated in the top plate 478. The plates 476 and 478 are integrated with the microscope system frame 205 for supporting the camera 105 and the lens 110.

The motor controller 485 is connected to the z-axis motor 150 to provide control signals to adjust the height of the camera 105 and lens 110 for adjusting the 3D effect. The motor controller 485 receives control signals externally from the footswitch 495. These signals determine the amount of movement along the z-axis the camera makes in focusing the lens 110.

The light controller 480 receives external control signals that determine the intensity of the lighting created by the illumination apparatus 175 and targeted upon the medical/ surgical specimen 185. The illumination apparatus 175 will be described in greater detail hereinafter.

Referring now to FIG. 11B, the 2D microscope 400 is mounted to an articulated arm 405. The articulated arm 405 is secured to the adjustable pole 410. The adjustable pole 410 securely affixed to a weighted base 415 that allows the articulated arm 405 to move horizontally, vertically, and rotationally about the horizontal and vertical axes. Further, the 2D microscope 400 is mounted to the articulated arm such that it can rotate about the axis of the articulated arm 405. This allows the 2D microscope 400 to point such that the camera 105 can capture images pointing upward or downward or horizontally in any direction. The cabling of the 2D microscope 400 is fed through the interior of the articulated arm 405 and the adjustable pole 410. The power cabling 102 for the LED illumination apparatus 175 and the USB cable 103 are fed from the adjustable pole to the light controller 480 and the image processor 490. The image captured by the camera 105 of the 2D microscope 400 is processed by the image processor 490 and displayed on the monitor 265. The lighting is adjusted by the light controller 480 such that LED illumination apparatus 175 provides sufficient light for the medical/surgical sample being examined.

FIG. 12A is a diagram of a top view and FIG. 12B is a diagram of a bottom view of an LED illumination apparatus 175 within a 3D microscope system 100, and 300 embodying the principles of the present disclosure. FIG. 12A shows the top view of the LED illumination device 175. The case 340 a cylindrical shape that is configured to contain the multiple LED lamps 345. The multiple LED lamps 345 are held in place with the retention ring 355. The retention ring 355 is further secured to the case with circular insert 356 that is fastened to the case 340 to hold the retention ring 345 in place and thus secure the multiple LED lamps 345. The case 340 is formed of a material such as steel (stainless or carbon), aluminum, fiberglass, polycarbonate, polyamide, polystyrene, or other suitable organic polymers. The retention ring 355 may be a metal such as steel or aluminum to provide a level of heat sinking for the multiple LED lamps 345. The connections to the multiple LED lamps 345 are made through the top with a connector fashioned into the case 340 as convenient for the design. The view of the multiple LED lamps 345, as shown in FIG. 12A is showing a heat sink structure that is in contact with the retention ring 355 for added cooling capacity.

FIG. 12B shows the bottom view of the multiple LED lamps 345. The multiple LED lamps 345 are connected to a wiring raceway 347 to which the external wiring for the multiple LED lamps 345 is fed and through which the multiple LED lamps 345 are adhered. The wiring raceway is affixed to the case 340 to secure the multiple LED lamps 345 in place. The opening 350 provides a camera window such that the lens of the camera is in view with the medical/surgical specimen 185 of FIGS. 1, 7A, 7B, 8, 10, and 11A.

FIGS. 13A, 13B, and 13C are diagrams of an LED lamp 345a used in the LED illumination apparatus 175 of FIGS. 12A and 12B embodying the principles of the present disclosure. FIGS. 13A and 13B illustrate two embodiments of the LED lamps 345a that are used in the LED illumination apparatus of FIGS. 12A and 12B. The LED lamp 345a has an LED device 345b of FIG. 13C housed a circuit packaged in a casing 345d. The LED device 345b has wiring leads 345c that are led from the casing 345d. A lens 345e is placed at an opening of the casing 345d and 345d such that light from the LED device 345b can leave the casing 345d. The lens 345e may be designed such that the light is focused for concentration at a point such as the medical/surgical specimen 185. The wiring leads 345c as led from the casing 345d are connected with power cabling in the wiring raceway 347 of FIG. 12B. Heatsinks 345f-1 and 345f-2 are connected to the casing 345d for cooling of the LED device 345b. The heat sink 345f-1 is physically larger and configured with a coefficient of thermal resistance to provide better cooling for the LED device 345b and therefore allowing for greater heat generation and brighter light from the LED device 345b. The heat sink 345f-2 is physically smaller and configured with a coefficient of thermal resistance to provide less cooling for the LED device 345b and therefore allowing for less heat generation and less bright light from the LED device 345b.

Figure 14:
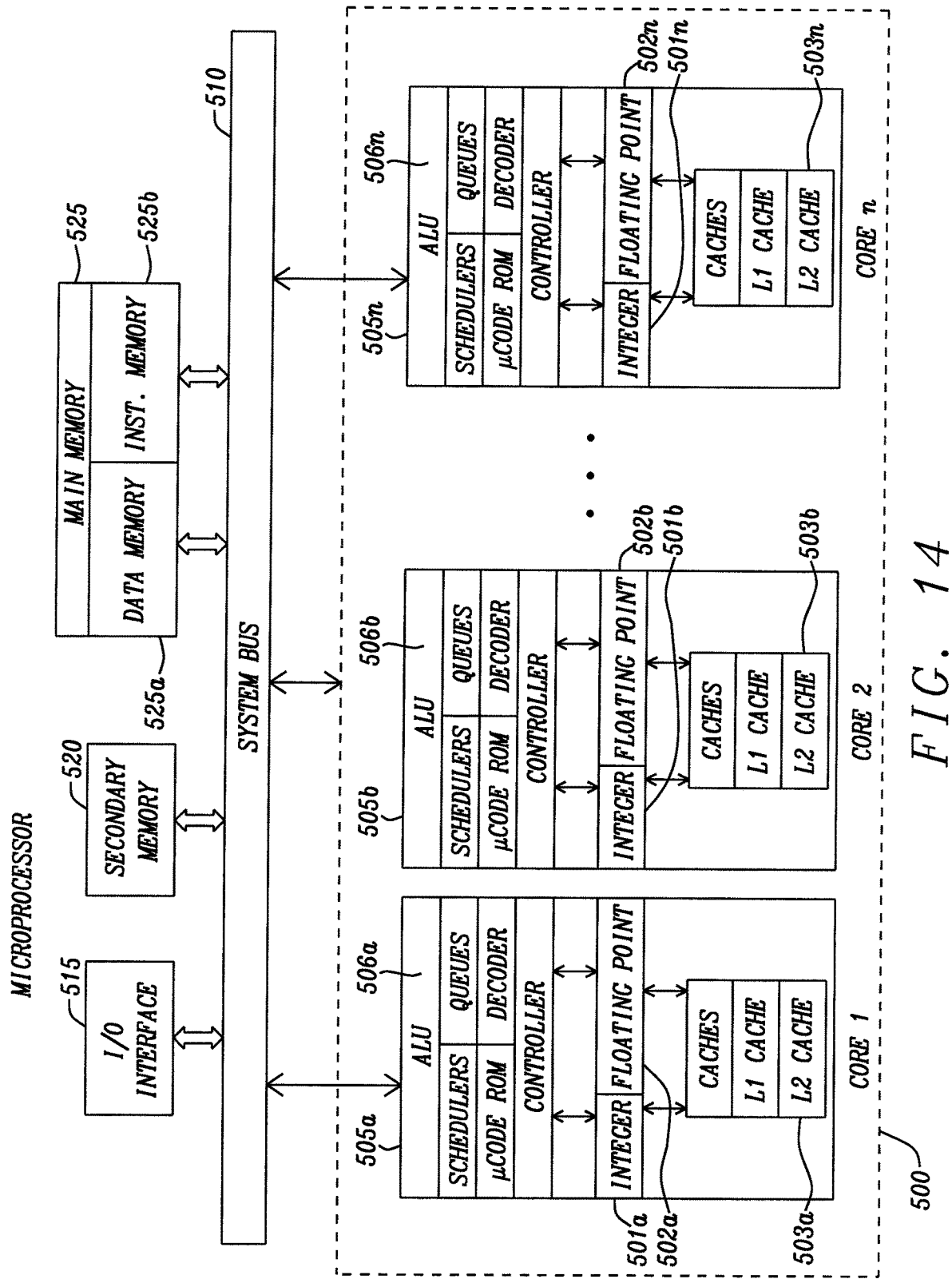
FIG. 14 is a block diagram of an exemplary multi-core processor of an image processor embodying the principles of the present disclosure.

FIG. 14 is a block diagram of an exemplary multi-core processor 500 of an image processor embodying the principles of the present disclosure. The image processor 160 of FIG. 1, 390 of FIGS. 8 and 10, 490 of FIGS. 11A and 11B are shown as a multicore microprocessor 500 such those marketed by Intel Corporation, Santa Clara, Calif. 95054, and Advanced Micro Devices, Arm Global Holdings plc, Cambridge, CB1 9NJ, United Kingdom. The microprocessor 500 has multiple processor cores 505a, 505b, . . . , 505n integrated within a single semiconductor substrate. The image processor 160 of FIG. 1, 390 of FIGS. 8 and 10, 490 of FIGS. 11A and 11B has an input/output interface circuit 515 that receives the image data streams transferred on the USB cable 103 of FIGS. 1, 10, 11A, and 11B, and 16. Upon completion of the processing of the 2D image data streams by the image processor 160 of FIG. 1, 390 of FIGS. 8, 10 and 16, 490 of FIGS. 11A and 11B, the 2D images of FIGS. 11A and 11B and the 3D images of FIGS. 1, 8, 10, 16 are transferred to the display 165 of FIGS. 1, 8, 10, and 16 and 2D images are transferred to the display 265 of FIGS. 11A and 11B. The I/O interface 515 is in communication with the secondary memory 520 and the main memory 525 for transferring data including the 2D image data from the camera and the processed image data to and from the secondary memory. The data may also be any program instruction data stored in secondary memory. The secondary memory includes mass relatively slow temporary data storage devices and permanent non-transitory storage devices such as solid state, magnetic and optical storage.

The main memory 525 is a volatile memory that has a large number of Random Access Memory (RAM) modules configured into memory banks. In most present implementations of the main memory 525, the RAM modules are either static (SRAM) or dynamic (DRAM) RAM memory modules. The main memory may be divided into a data memory 525a and an instruction memory 525b. The instruction memory 525b retains the program instruction data that the image processor executes for converting the image data from the cameras 105 into the 2D and 3D image data for presentation on the 3D display 165 of FIGS. 1, 8, 10, and 16 and the 2D display 265 of the FIGS. 11A and 11B. The data memory 525a retains the data for processing by the multiple processor cores 505a, 505b, . . . , 505n of the microprocessor 500. The main memory 525 has a memory controller that receives the image data from the camera(s) 105 of the 3D and 2D microscopes. The memory controller assigns the image data to memory arrays within the DRAM modules. Further, the memory 525 is in communication with the permanent secondary memory 520 for retention of the video frame data pending processing and the processed 3D frame data after processing.

Each of the multiple processor cores 505a, 505b, . . . , 505n are configured with an arithmetic logic unit (ALU) 506a, 506b, . . . , 506n. Each ALU 506a, 506b, . . . , 506n has a μcode read only memory that stores the initiating operating program code for the ALU's 506*a*, 506*b*, . . . , 506*n*. Upon initiation of the ALU's 506*a*, 506*b*, . . . , 506*n*, the controller is instructed to request the program instruction data from the instruction memory 525*b*. The program instruction data is decoded by the decoder and instructions are scheduled within the scheduler and place in the queues. The image data is requested from the data memory 525*a* and placed in the caches 503*a*, 503*b*, 503*n*. Based on the priority of the data, the data will be placed in either the L1 or L2 data cache. Based on the program procedure for processing the 2D image data to the 3D image data, the controller will command the integer unit 501*a*, 501*b*, . . . , 501*n* or the floating point unit 502*a*, 502*b*, . . . , 502*n* to process the 2D image data to generate the 3D image data for display. The program procedure for processing the 2D image data to the 3D image data will be discussed hereinafter. The processed 3D image data is returned to the caches 503*a*, 503*b*, . . . , 503*n*, then transferred to the data memory 525*a* for presentation on the 3D display 165 of FIGS. 1, 8, 10, and 16 and the 2D display 265 of the FIGS. 11A and 11B. After the initial presentation of the processed 3D image data, the processed 3D image data may be then transferred to the secondary storage 520 for permanent retention.

Figure 15:
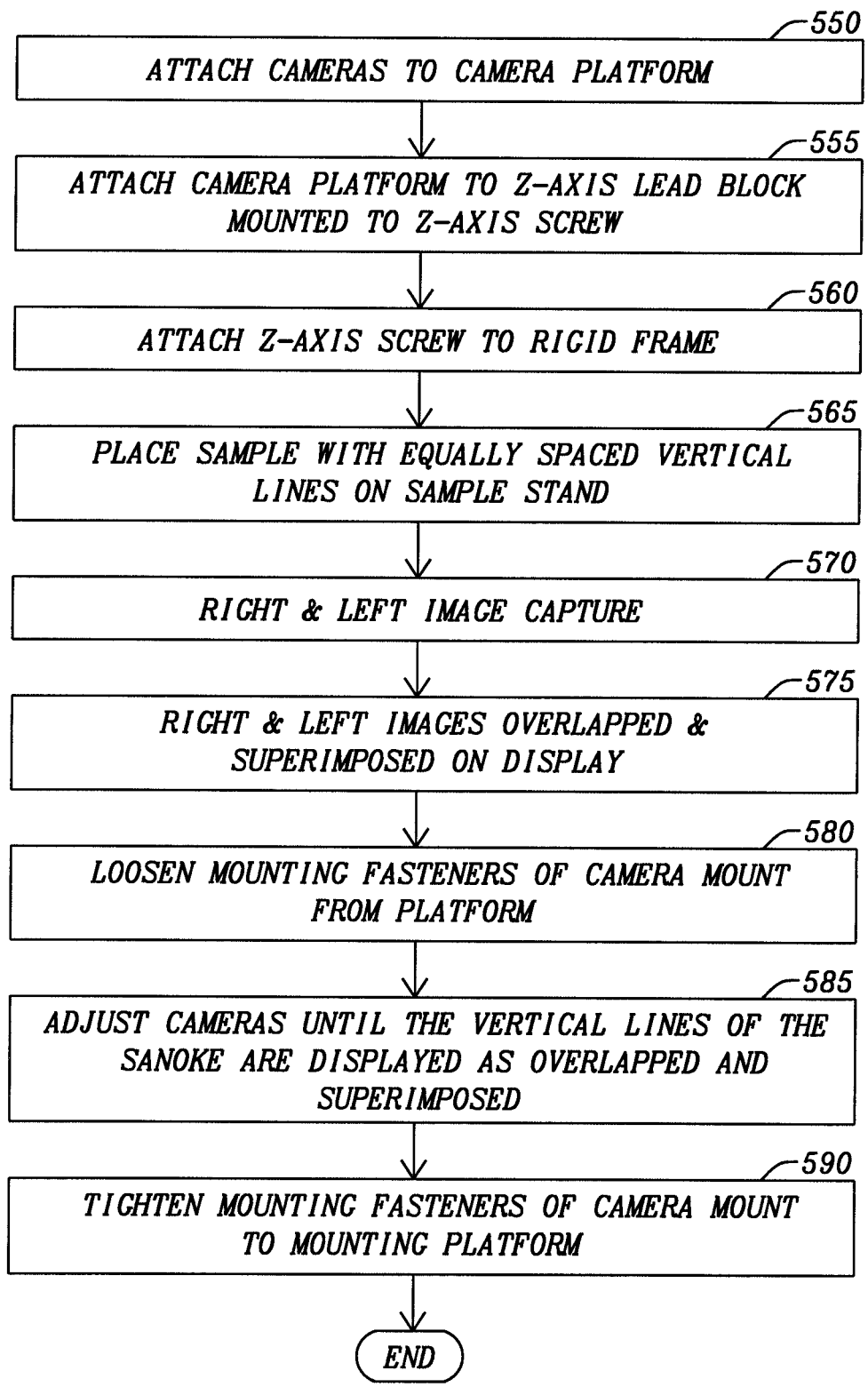
FIG. 15 is a flow chart for a method of aligning the images of the cameras of the 3D microscope system embodying the principles of the present disclosure.
Figure 16:
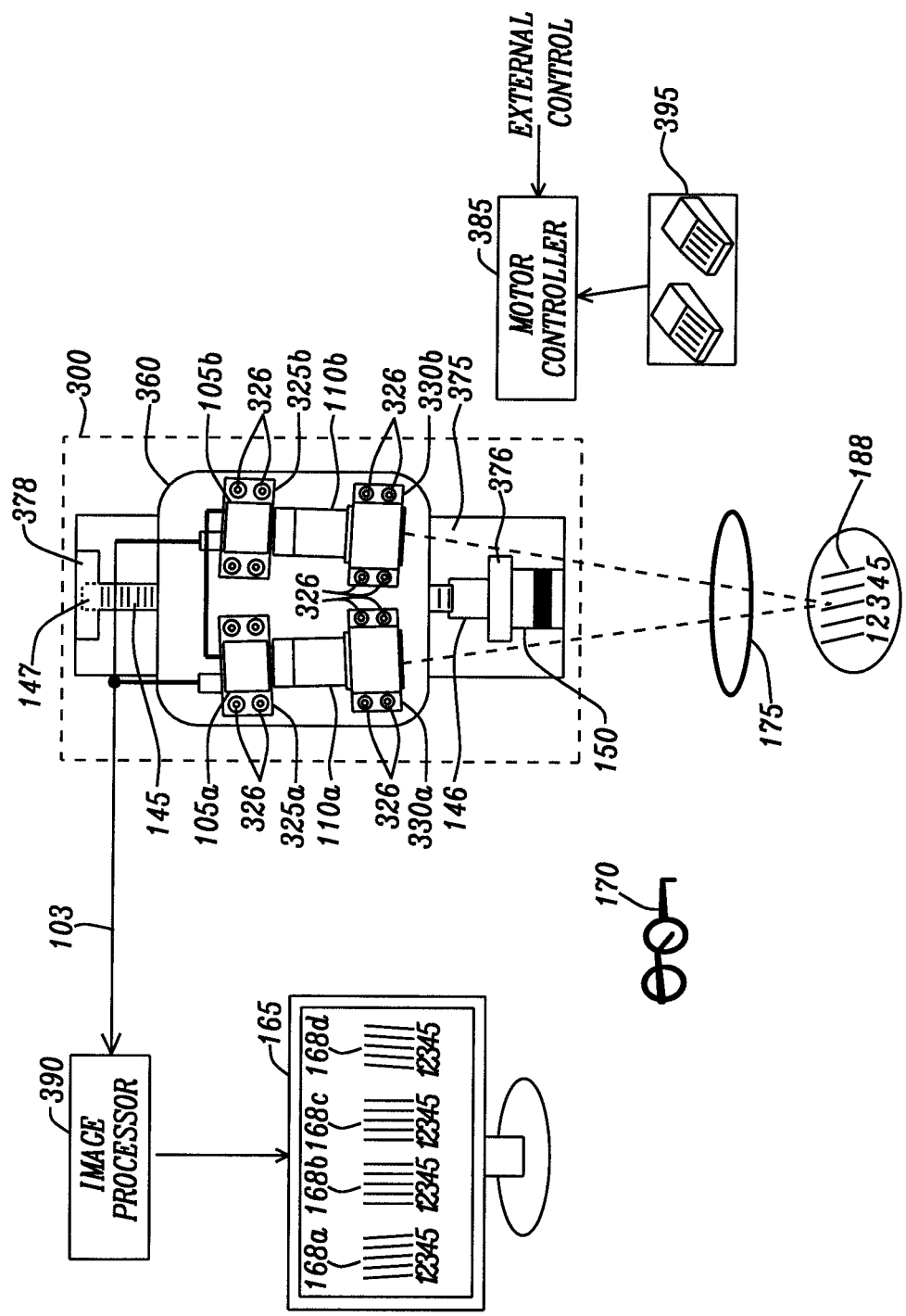
FIG. 16 is a structural diagram illustrating the aligning of the images of the cameras of the 3D microscope system embodying the principles of the present disclosure.

FIG. 15 is a flow chart for a method of aligning the images of the cameras 105*a*, 105*b* and lenses 110*a*, 110*b* of the 3D microscope system 300 embodying the principles of the present disclosure. FIG. 16 is a structural diagram illustrating the aligning of the images of the cameras of the 3D microscope system 300 embodying the principles of the present disclosure. The cameras 105*a*, 105*b* and lenses 110*a*, 110*b* of the 3D microscope system 300 must be calibrated such that the images projected by the two cameras 105*a*, 105*b* are aligned on the video monitor 165. Referring to FIGS. 15 and 16, the cameras 105*a*, 105*b* and lenses 110*a*, 110*b* are attached (Box 550) to the camera platform 360. The camera platform 360 is attached (Box 555) to a lead block (not visible but shown as feature 200 in FIG. 4) that is mounted to a z-axis screw 145. The z-axis motor 150 is connected to the z-axis leadscrew 145 through a bottom z-axis bearing 146. Please note that the z-axis screw 145 is inverted to that shown in FIG. 1. The inversion of the z-axis leadscrew may shorten the physical height of the 3D microscope system 300 by placing the z-axis motor 150 under the camera platform 360. The bottom z-axis bearing 146 is attached to the bottom plate 376. The top plate 378. The bottom plate 376 and the top plate 378 are attached to the microscope system frame 375 that is attached (Box 560) to a rigid frame similar to the support apparatus 215 of FIGS. 7A and 7B. The support apparatus 215 is secured to a pair of vertical rails 210 through openings in the support apparatus 215, as in FIGS. 7A and 7B.

A test sample 188 is structured with a set of equal length parallel lines. The test sample is placed (Box 565) on the sample stand. The sample stand in some embodiments is the sample stand 225 of FIGS. 7A and 7B. The sample stand or bottom stand 225 has a support block 227 that connects the vertical rails 210 to the sample stand 225 for supporting the rigid frame.

The cameras 105*a* and 105*b* are activated to capture (Box 570) the image of the test sample 188. The captured images are transferred to the image processor 390. The image processor 390 is executing its program process in "alignment mode". The images 168*a*, 168*b*, 168*c*, and 168*d* from both cameras 105*a* and 105*b* are displayed (Box 575) on the monitor 165 such that they are overlapped and superimposed to assist calibration. Because of misalignment from cameras 105*a* and 105*b* or camera mounts 325*a*, 325*b*, 330*a*, 330*b*, images 168*a* and 168*d* from both cameras 105*a* and 105*b* are usually rotated and shifted along the vertical axis.

The threaded fasteners 326 that fit into the openings of the camera mounts 325*a*, 325*b*, 330*a*, 330*b* for securing the cameras 105*a*, 105*b* and lenses 110*a*, 110*b* to the camera platform 360 are loosened (Box 580). The cameras 105*a*, 105*b* and lenses 110*a*, 110*b* are adjusted (Box 585) until the vertical lines 1, 2, 3, 4, and 5 are displayed as overlapped and superimposed. The threaded fasteners 326 are tightened (Box 590) to secure the cameras 105*a*, 105*b* and lenses 110*a*, 110*b* to the camera platform 360.

The image processor 390 further includes a non-transitory memory device that is readable by the multiple processor cores of the image processor 390. The non-transitory memory device has a program of instructions stored on it that is executable by the multiple processor cores to perform a program process for calibrating the alignment of the images 168*b* and 168*c*, when the threaded fasteners are tightened (Box 590) and is discussed hereinafter.

The flow chart of FIG. 15 is equally applicable to aligning the images of the cameras 105*a*, 105*b* and lenses 110*a*, 110*b* of the 3D microscope system 100 of FIG. 1. Referring to FIG. 1, the cameras 105*a*, 105*b* and lenses 110*a*, 110*b* are attached (Box 550) to the two camera mounts 115*a* and 115*b* as described above. The two camera mounts 115*a* and 115*b* are then in turn coupled to one of the two rotary tables 120*a* and 120*b*. The two rotary tables 120*a* and 120*b* are rotated such that each of the two camera mounts 115*a* and 115*b* and therefore each of the two digital cameras 105*a* and 105*b* and the two lenses 110*a* and 110*b* are pointed at a common point of the medical/surgical specimen 185.

The two rotary tables 120*a* and 120*b* are secured (Box 550) to a mounting platform 125 through the rotating table bearing 121 that allows the two rotary tables 120*a* and 120*b* and thus the two digital cameras 105*a* and 105*b* and the two lenses 110*a* and 110*b* to be rotated. Each of the two camera mounts 115*a* and 115*b* is coupled to one of the two camera mount leadscrews 130*a* and 130*b* through a spring lead block and the open slit-leg 116*a*, 116*b* of FIG. 3. The two camera mount leadscrews 130*a* and 130*b* are each connected to a camera mount adjustment motor 135*a* and 135*b* adjust the angle of each of the two cameras 105*a* and 105*b* and lenses 110*a* and 110*b*, independently, as shown in FIG. 1.

The z-axis motor 150 is connected to the z-axis leadscrew 145 through a top z-axis bearing 146. The top z-axis bearing 146 and a bottom z-axis bearing 147 (reversed from FIG. 16) are secured (Box 560) to the rigid frame stand. The top z-axis bearing 146 and a bottom z-axis bearing 147 allow the z-axis leadscrew 145 to be turned freely by the z-axis motor 150. The z-axis lead block 200 of FIG. 4 is threaded onto the z-axis leadscrew 145 and fastened to the mounting platform 125 to adjust the height of the cameras 105*a* and 105*b* and lenses 110*a* and 110*b* for adjusting the 3D effect on the monitor.

The method continues as described above. The fasteners that are loosened (Box 580) in this embodiment are as shown in FIG. 5A, where the fasteners 118*a* placed in the openings 118*b* in the camera mount 115 as shown in FIG. 5B. The process continues with the adjustment (Box 585) of the sample images 168*b* and 168*c* and the tightening (Box 590) of the fasteners 118*a*.

Figure 17:
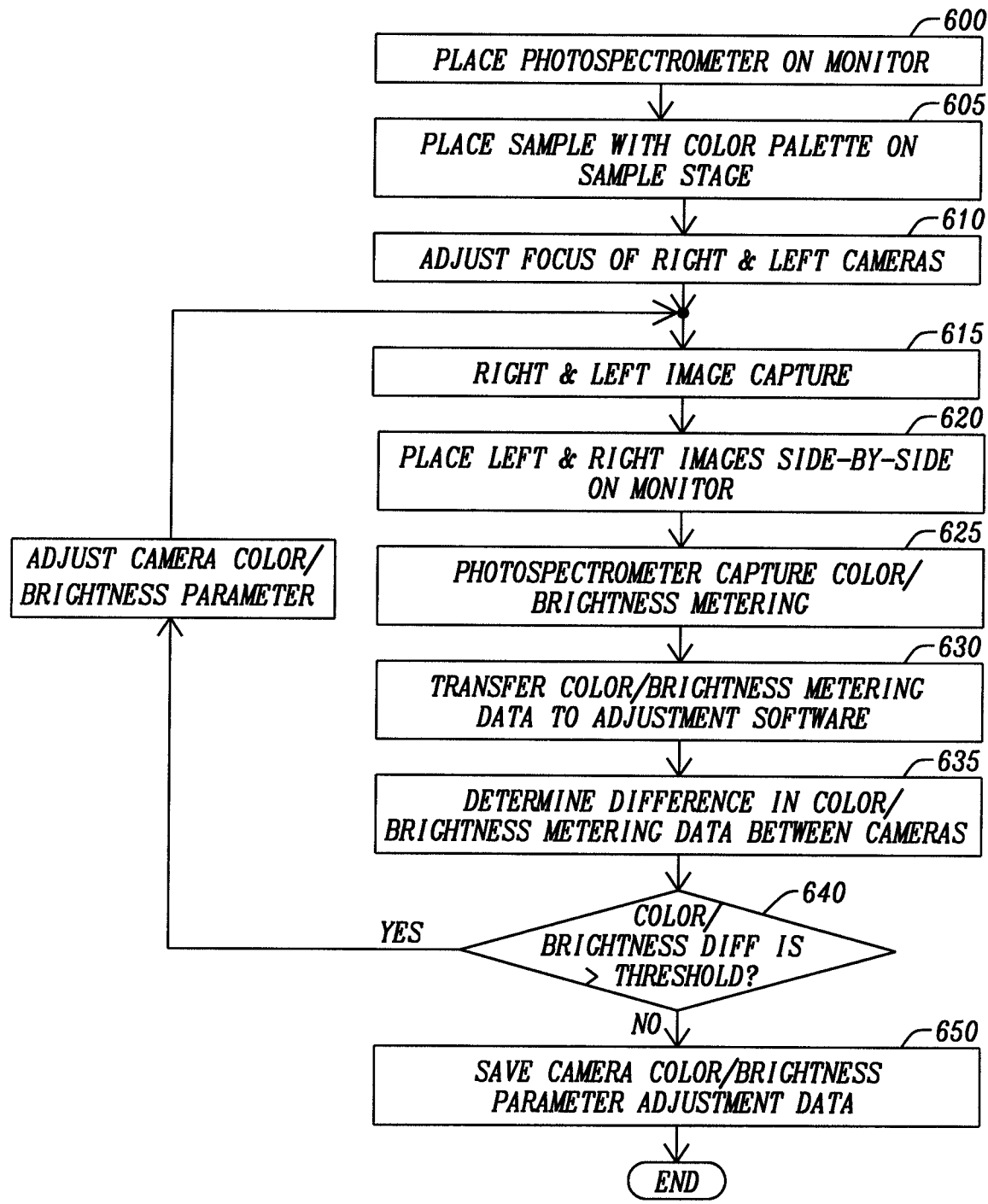
FIG. 17 is a flow chart of a method for color/brightness equalization by adjusting camera color/brightness parameters of the cameras of the 3D microscope system embodying the principles of the present disclosure.
Figure 18:
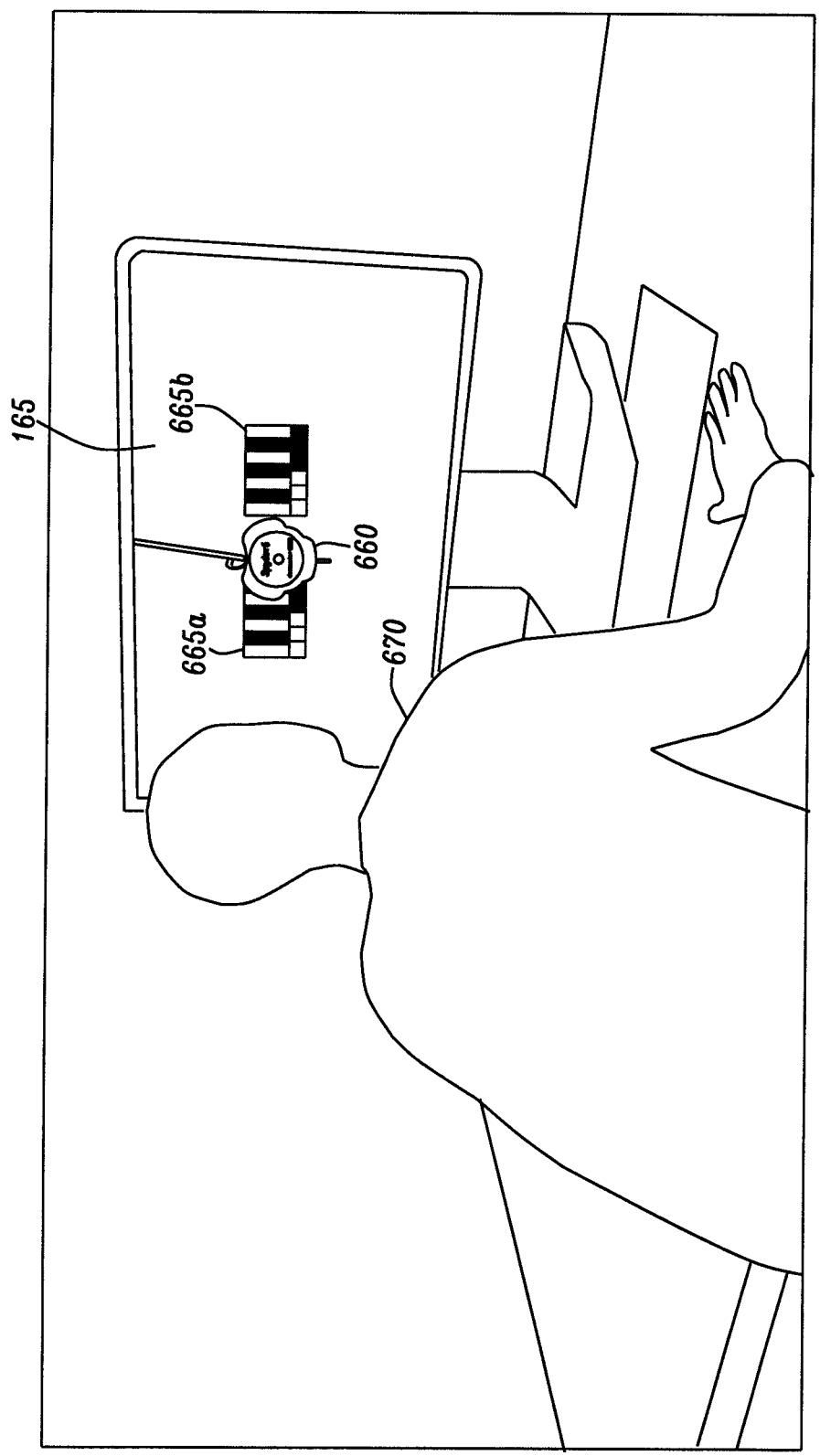
FIG. 18 is a diagram of a person performing the color/brightness equalization method of FIG. 17 on the 3D microscope system embodying the principles of the present disclosure.

The final calibration of the 3D microscope system 100, 200 is the adjustment of the camera color/brightness parameters of the cameras 105*a* and 105*b*. FIG. 17 is a flow chart of a method for color/brightness equalization by adjusting camera color/brightness parameters of the cameras 105*a* and 105b of the 3D microscope system 100, 200 embodying the principles of the present disclosure. FIG. 18 is a diagram of a person performing the color/brightness equalization method of FIG. 17 on the 3D microscope system 100, 300 embodying the principles of the present disclosure. The method for adjustment of the color/brightness equalization begins with the placing (Box 600) of a photospectrometer 660 on the monitor 165. The spectrophotometer 660 is an optical instrument for measuring the intensity of light relative to wavelength.

A sample is placed (Box 605) on the sample stand such as the sample stand 225 of FIGS. 7A and 7B. The sample will be a calibrated image of the color palette. The focus of the cameras 105a and 105b and lenses 110a and 110b is adjusted (Box 610) and the image is captured (Box 615) by the cameras 105a and 105b. The left and right images 665a and 665b of the color palette are displayed (Box 620) sequentially in turn on the monitor 165. The photospectrometer 660 captures (Box 625) the color and brightness of the left and right color palette images 665a and 665b. The image processor 390 of FIG. 16 is programmed to execute a program process for adjusting the color and brightness intensity settings of each of the cameras 105a and 105b. The spectrophotometer 660 transfers (Box 630) the captured readings of the color and brightness intensity to the color/brightness adjustment program process. The color/brightness adjustment program process determines (Box 635) the difference of the color and brightness intensity between the cameras 105a and 105b. The color/brightness adjustment program process then compares (Box 635) the difference of the color and brightness intensity between the cameras 105a and 105b with a predetermined threshold. If the difference of the color and brightness intensity between the cameras 105a and 105b is greater than the predetermined threshold, the color/brightness adjustment program process adjusts (Box 640) each of the cameras 105a and 105b color/brightness parameters.

The image is again captured (Box 615) by the cameras 105a and 105b. The left and right images 665a and 665b of the color palette are displayed (Box 620) side-by-side on the monitor 165. The photospectrometer 660 captures (Box 625) the color and brightness of the left and right color palette images 665a and 665b. The spectrophotometer 660 transfers (Box 630) the captured readings of the color and brightness intensity to the color/brightness adjustment program process. The color/brightness adjustment program process determines (Box 635) the difference of the color and brightness intensity between the cameras 105a and 105b. The color/brightness adjustment program process then compares (Box 635) the difference of the color and brightness intensity between the cameras 105a and 105b with the predetermined threshold. When the difference of the color and brightness intensity between the cameras 105a and 105b is less than the predetermined threshold, the color/brightness parameter adjustment data is saved (Box 645) to a non-transitory non-volatile memory, thus completing the program process.

Figure 19:
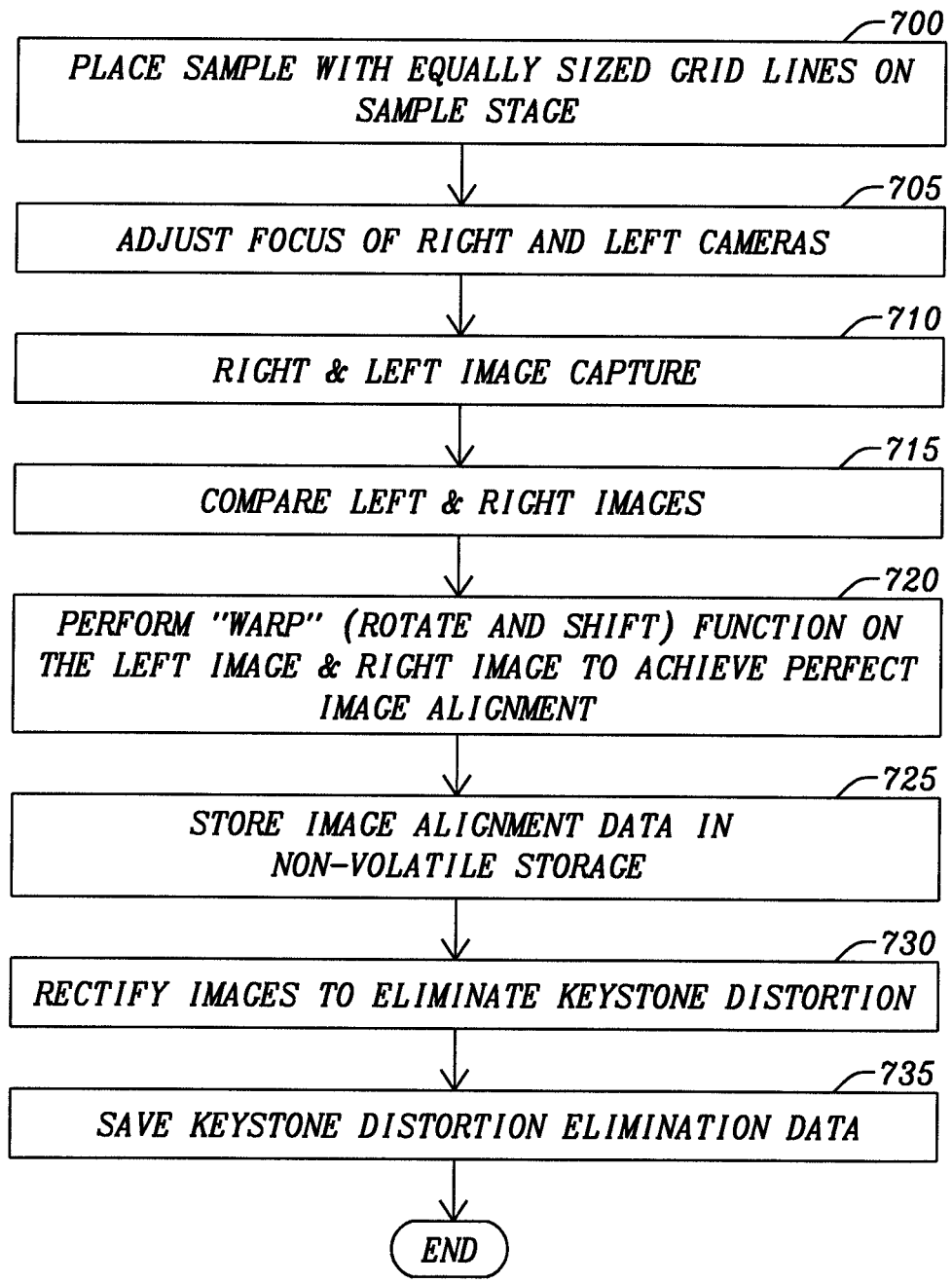
FIG. 19 is a flow chart of a method of rectification of keystone distortion due to toe-in of the cameras of the 3D microscope system embodying the principles of the present disclosure.

FIG. 19 is flow chart of a method of rectification of keystone distortion due to toe-in of the cameras 105a, 105b and lenses 110a, 110b of the 3D microscope system 100 300 embodying the principles of the present disclosure. Keystone correction for stereoscopic cinematography," Liu, et al., 2012 IEEE Computer Society Conference on Computer Vision and Pattern Recognition Workshops, 2012, pp.: 1-7 found May 17, 2019 at http://ieeexplore.ieee.org/stamp/stamp.jsp?tp=&arnumber=6238901&isnumber=6238883 describes keystone distortion as a long-standing problem in stereoscopic cinematography. Keystone distortion occurs when cameras 105a, 105b and lenses 110a, 110b toe in to achieve a desirable disparity distribution. Vertical disparity is a particular problem from keystone distortion that may compromise the 3D viewing experience.

FIG. 20A is a graph of the geometry for the causes of the keystone distortion due to the toe-in of the cameras 105a, 105b and lenses 110a, 110b of the 3D microscope system 100, 300 embodying the principles of the present disclosure. FIG. 20b is a graph of the rectification of keystone distortion due to toe-in of the cameras 105a, 105b and lenses 110a, 110b of the 3D microscope system 100, 300 embodying the principles of the present disclosure. Referring to FIG. 20A a 3D scene point P is projected onto the left and right cameras 105a, 105b as the images $I^l$ and $I^r$ such that the left and right x-coordinates $X^l$ and $X^r$ of the scene point P are different. Their difference $(X^l-X^r)$ is referred to as (horizontal) disparity. The cameras 105a, 105b and lenses 110a, 110b of the 3D microscope system 100, 300 have two important parameters. The first is the baseline BL between the two cameras 105a, 105b optical centers and the second is the toe-in angle θ. However, camera toe-in leads to the keystone effect on images 740a and 745a as shown in FIG. 20B. The keystone correction is executed to transform the images 740a and 745a to the corrected images 740b and 745b.

Referring to FIG. 19, the keystone correction begins with placing (Box 700) sample with equally sized grid lines such as those shown in the image 740b and 745b of FIG. 20B on the sample stand such as the sample stand 225 of FIGS. 7A and 7B. The focus of the cameras 105a, 105b and lenses 110a, 110b is adjusted (Box 705) and the images of the sample are captured (Box 710). The program process for the keystone correction is retained in the non-transitory memory device that is readable by the multiple processor cores of the image processor 390 and begins with comparing (Box 715) both images 740a and 745a. The program process then performs (Box 720) a "warp" (rotate and shift) function on the images for perfect image alignment. The program process then stores (Box 725) the calibration data on non-transitory, non-volatile storage for later use. The images 740a and 745a are rectified (Box 730). In Lin, et al., a keystone correction method eliminates the undesirable vertical disparities and preserves the desirable (horizontal) disparities. Feature point P correspondences are estimated between the left and right view of both images 740a and 745a. Then the vertical disparity between each pair of feature points P is eliminated by assigning the average vertical coordinate to both points P. The horizontal disparities unchanged. Each input image is divided into a uniform grid mesh and the image warping is formulated as a mesh warping problem. The position constraints are encoded as data terms. The energy terms are carefully defined to be quadratic. The warping problem is thus quadratic and is solved using a standard linear solver. The keystone elimination encoded data terms are then saved (Box 735) for essentially real time keystone elimination.

FIG. 21 is a flow chart of a method for converting 2D microscope image data into 3D microscope image data for display on a 3D monitor included as part of the 3D microscope system embodying the principles of the present disclosure. The method begins with activating (Boxes 800 and 805) the cameras 105a and 105b of FIG. 1 for capturing (Boxes 810 and 815) the left and right frames to a frame pair. The left image frame and the right image frame are formatted (Boxes 820 and 825). The formatting (Boxes 820 and 825) performs a resizing or converting the left and right images to a 3D monitor 165 conforming format. The monitor 165 conforming formats are for example High-Definition Multimedia Interface (HDMI), VESA DisplayPort, or a Digital Visual Interface (DVI) or any other monitor 165 conforming formats known in the art.

The left image frame and the right image frame are conditioned (Boxes 830 and 835). The conditioning (Boxes 830 and 835) are program processes stored in non-transitory memory within the image processor 390 of FIG. 16 such that when executed performs image calibration/rectification and color/brightness equalization for a better match of the image frames. The conditioning program process extracts the image calibration data for calibrating the left and right images 168b and 168c. The image distortion of the keystone effect is rectified and color/brightness difference among the cameras 105a, 105b are resolved and equalized.

Figure 22E:
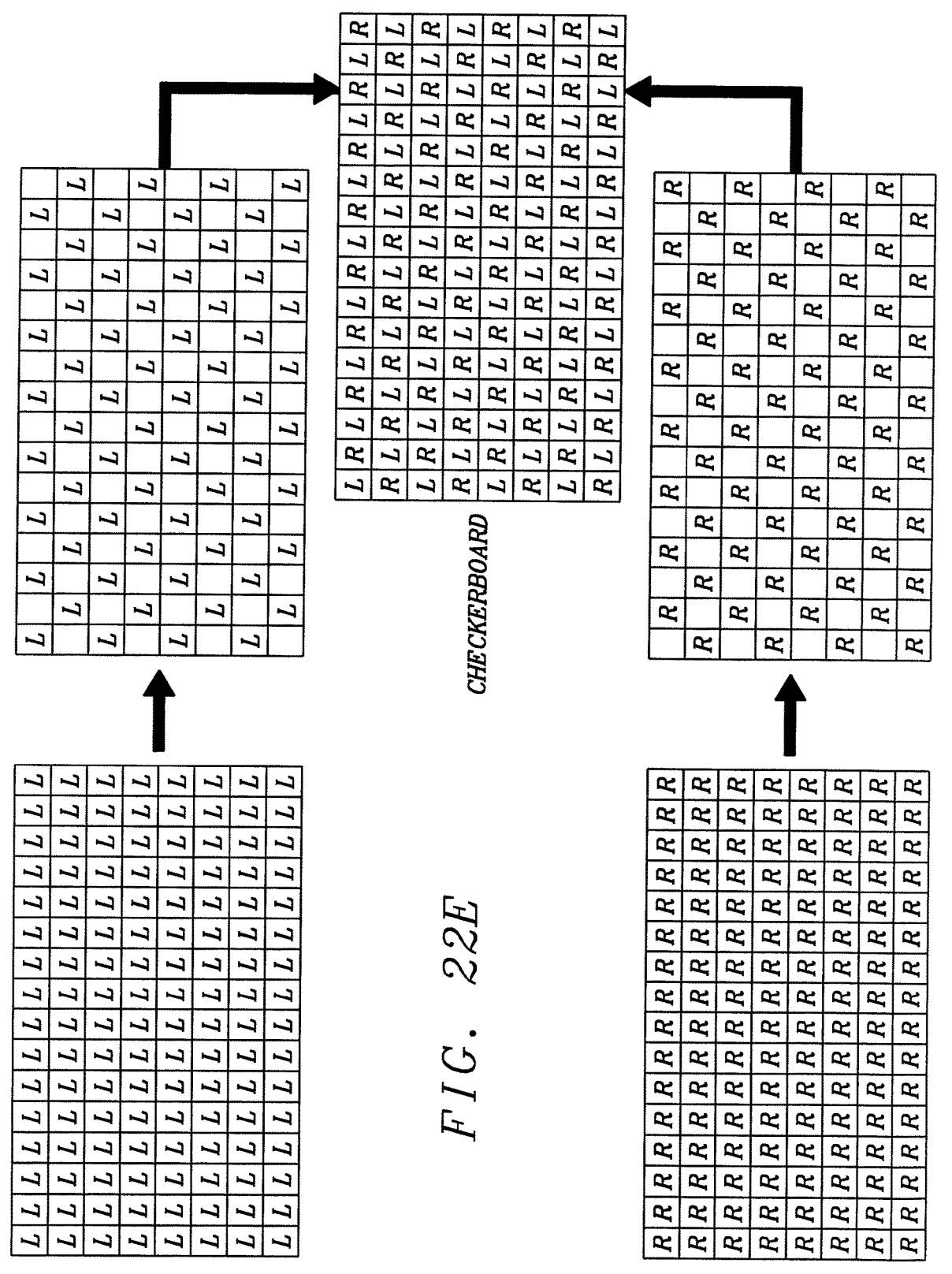

The left image frame and the right image frame from the cameras 105a, 105b are combined (Box 840). The combining (Box 840) merges left and right image frames of the cameras 105a, 105b to create an image that conforms to the 3D image formats of the 3D monitor 165. FIGS. 22A-22E are diagrams of the video monitor 165 of FIG. 16 frame formats after combining the cameras 105a, 105b video images of the 3D microscope system 100, 300 embodying the principles of the present disclosure. For this discussion, the implementation of each of the cameras 105a, 105b has an initial resolution of 1920 pixels horizontally ×1080 pixels vertically. Depending on which 3D format that is chosen, the images are further processed to create a new image that conforms to one of the 3D monitor formats. In FIG. 22A the format is a frame sequential or temporal multiplexing on each frame from the cameras 105a, 105b. The left and right images from the cameras 105a, 105b would be interleaved as alternating frames or fields. The frame rate of each image may be reduced such that the amount of data is equivalent to that of a single image.

FIG. 22B illustrates a "Side-by-Side (SbS)" format. In the SbS format, the left and right from the cameras 105a, 105b are decimated horizontally such that each image is now 960 pixels horizontally and 1080 pixels vertically. The left and right images are stored in side-by-side in each frame such that the frame has the left and right images in a frame of 1920 pixels horizontally and 1080 pixels vertically. The monitor has a processor that will extract the two images and restore the resolution for the display.

FIG. 22C illustrates a Top-and-Bottom (TaB) format. In the TaB format, the left and right images from the cameras 105a, 105b decimated from the top into a format 1920 pixels horizontally and 540 pixels vertically. The left and right images of the cameras 105a, 105b are stored top and bottom in each frame such that the frame has the left and right images formed into an image having 1920 pixels horizontally and 1080 pixels vertically.

FIG. 22D illustrates a Line-by-Line (LbL) format. In the LbL format, the odd horizontal lines from one set of the images of the cameras 105a, 105b are extracted and even horizontal lines from the other set of the images of the cameras 105a, 105b. Each set of the lines has a pixel density of 1920 horizontal pixels by 540 vertical pixels. These odd/even lines of the pixels of the images are then interleaved into a new 1920 horizontal pixel by 1080 vertical pixel image. The monitor will display each line and the view will have a pair of glasses that will alternately display the sets of interleaved vertical pixels to create the final 3D image.

FIG. 22E illustrates a "Checkerboard" format. The checkerboard pattern is a quincunx pattern where each image from the cameras 105a, 105b is decimated horizontally by a factor of 2, with a one pixel shift toggling line by line, resulting in two 2D diagonal filtered and decimated images arranged together in a checkerboard-like output pattern. The encoded image pattern is generated by horizontal or vertical decimation of each image from the left and right cameras 105a, 105b with the two images superimposed on each other to form a single image that is 1920 horizontal pixels by 1080 pixels. When the encoded image is transferred to the monitor 165 the checkerboard image is decomposed to two separate images by the monitor 168 and then recombined to form the image on the monitor 168. Referring back to FIG. 21, the combined image is then transferred (Box 845) to the monitor 165 for display, FIG. 23 is a diagram of a parallel pipeline structure of the multi-core image processor 500 of FIG. 14 performing the method for converting 2D microscopic images into 3D microscopic images for display on a 3D display monitor 165 of FIGS. 1, 8, 10, 11, and 16 included as part of the 3D microscope system 100 and 300 embodying the principles of the present disclosure. The image processor 160 of FIG. 1, 390 of FIGS. 8 and 10 organizes the image processing pipeline that consists of the five stages of the method of FIG. 21, namely, capturing (Boxes 810 and 815), formatting (Boxes 820 and 825), conditioning (Boxes 830 and 835), 3D combination (Box 840), and transfer (Box 845) to the 3D display 165. The image frames must be processed through these five stages of the pipeline sequentially. A shared/dedicated process or thread is allocated for each stage to speed up the process by allocating one of the processes or thread to the I/O interface 515 and to one core processor 505a, 505b, and 505c. The first process is allocated to the I/O processor 515 for receiving the image data from the cameras 105a and 105b. The second through fourth processes is allocated to the core processors 505a, 505b, and 505a. The fifth process is allocated to the I/O interface for displaying the image on the display 165.

The parallel-pipeline of executing the stages of the processes begins to fill with the initiation of the cameras 105a and 105b and the capturing of the image data transferred from the cameras 105a and 105b to the I/O interface 515. The I/O interface 515 transfers the video image to assigned locations in the secondary storage 520 and to the main data storage 525a. The data is then transferred to the first processor core 505a for formatting. At the second time slot, the first frame data is transferred to the second processor core 505b for conditioning and a second frame data is transferred from the cameras 105a and 105b to the I/O interface 515 and thus to secondary storage 520 and the main data storage 525a. At the third time slot, the first image data is transferred to the second processor core 505b for conditioning and the second image data is transferred the first processor core 505a for formatting. A third frame data is captured from the cameras 105a and 105b to the I/O interface 515. The I/O interface 515 transfers the third frame data to assigned locations in the secondary storage 520 and to the main data storage 525a.

At the fourth time slot, the first frame data is transferred to the third processor core 505c for the combining of the 2D frame data to be the 3D frame data and the second image data is transferred the second processor core 505b for conditioning. The third frame data is transferred to the first processor core 505a for formatting. The fourth frame data is captured from the cameras 105a and 105b to the I/O interface 515. The I/O interface 515 transfers the third frame data to assigned locations in the secondary storage 520 and to the main data storage 525a.

At the fifth time slot, the first frame data is transferred to main data memory 525a and thus to the I/O interface 515 and thus to the display 165 for viewing. At the same time, the first frame data will be transferred to the secondary storage 520 to be retained for future view and analysis. The second image data is transferred to the third processor core 505c for the combining of the 2D frame data to be the 3D frame data and the third image data is transferred the second processor core 505b for conditioning. The fourth frame data is transferred to the first processor core 505a for formatting. The fifth frame data is captured from the cameras 105a and 105b to the I/O interface 515. The I/O interface 515 transfers the third frame data to assigned locations in the secondary storage 520 and to the main data storage 525a.

At the sixth time slot, the second frame data is transferred to main data memory 525a and thus to the I/O interface 515 and thus to the display 165 for viewing. At the same time, the second frame data will be transferred to the secondary storage 520 to be retained for future view and analysis. The third image data is transferred to the third processor core 505c for the combining of the 2D frame data to be the 3D frame data and the fourth frame data is transferred the second processor core 505b for conditioning. The fifth frame data is transferred to the first processor core 505a for formatting sixth frame data is captured from the cameras 105a and 105b to the I/O interface 515. The I/O interface 515 transfers the third frame data to assigned locations in the secondary storage 520 and to the main data storage 525a.

The process can be generalized as shown in the nth time slot, the nth frame data is transferred to main data memory 525a and thus to the I/O interface 515 and thus to the display 165 for viewing. At the same time, the nth frame data will be transferred to the secondary storage 520 to be retained for future view and analysis. The nth+1 image data is transferred to the third processor core 505c for the combining of the 2D frame data to be the 3D frame data and the nth+2 frame data is transferred the second processor core 505b for conditioning. The nth+3 frame data is transferred to the first processor core 505a for formatting. The nth+4 frame data is captured from the cameras 105a and 105b to the I/O interface 515. The I/O interface 515 transfers the nth+4 frame data to assigned locations in the secondary storage 520 and to the main data storage 525a.

Once the pipeline is filled, the process continues until the video recording of medical/surgical procedures is completed. The pipeline is then flushed and the program process is ended.

While this disclosure has been particularly shown and described with reference to the preferred embodiments thereof, it will be understood by those skilled in the art that various changes in form and details may be made without departing from the spirit and scope of the disclosure.

What is claimed is:

1. An apparatus configured to convert rotary motion to linear motion to angular motion for adjusting toe-in of a plurality of cameras within a multi-ocular optical system, comprising:
   an angle leadscrew assembly attached to a camera platform within the multi-ocular optical system for adjusting the angle of each of the plurality of cameras are directed to a common point of an observed object; wherein the angle leadscrew assembly comprises:
      a plurality of angle adjustment leadscrews wherein each angle adjustment lead screw is adapted for rotating,
      a plurality of spring lead block, wherein each spring lead block has a threaded, circular opening such that the spring lead block is threaded onto one angle adjustment leadscrew wherein the spring lead block has a routed opening into which a spring is secured,
      a plurality of fifth bearings wherein each of the fifth bearings is placed at one end of one angle adjustment leadscrew and secured to the support platform to permit rotation of the one angle adjustment leadscrew,
      a plurality of sixth bearings wherein each of the sixth bearings is placed at a second end of one angle adjustment leadscrew and secured to the camera to permit rotation of the angle adjustment leadscrew, and
      a plurality of angle adjustment motors wherein each of the angle adjustment motors is coupled to the fifth bearing and secured such that when the angle adjustment motor receives power the angle adjustment lead screw is rotated to adjust the angle of the camera mount and thus to adjust the toe-in of one camera of the plurality of camera; and
   a plurality of rotary tables wherein each rotary table is attached to the support platform.

2. The apparatus of claim 1 further comprising a plurality of lens mounts, wherein each camera of the plurality of camera is mounted to one of the plurality of camera mounts and wherein each camera mount comprises:
   a first plurality of threaded openings to accept threaded fasteners for securing one camera to the camera mount;
   a second plurality of threaded openings to accept threaded fasteners for securing the camera mount to one rotary table; and
   an open slit-leg attached to the camera mount at a lower side of the camera mount and placed between two coils of the spring of the spring lead block to set a maximum toe-in adjustment angle of the camera mount.

3. The apparatus of claim 1 wherein when the angle adjustment motor rotates the angle adjustment leadscrew of one lens, the toe-in angle of the lens is adjusted independently of the other lenses of the plurality lenses.

4. The apparatus of claim 2 further comprising a first motor controller connected to the z-axis motor for providing control signals to adjust the focus and convergence of the one or more cameras.

5. The apparatus of claim 2 further comprising a second motor controller connected to the angle adjustment motor for providing control signals to adjust the focus and convergence of the one or more cameras.

6. The apparatus of claim 2 wherein when the angle leadscrew assembly further comprises:
   one or more binding sensors attached to the camera platform and associated with each of the one or more camera mounts and configured for sensing that the associated camera mount is rotating beyond the fixed amount is approaching a point that the associated camera mount will bind the spring lead block; and
   one more sensor blades wherein each sensor blade is connected to one of the one or more spring lead blocks to sense the location of the spring lead blocks and thus the amount of the rotation of the associated camera mount, wherein each of the one or more sensor blades communicates the location of the spring lead block to an associated binding sensor such that when the binding sensor approaches the point at which the associated camera mount is approaching binding the spring lead block, the binding sensor transmits a binding signal to the second motor controller to issue a stop command to the camera mount adjustment motors to prevent damage to the angle adjustment leadscrew.

7. A method for calibrating a microscope system comprising the steps of:
provoking a microscope system comprising:
two digital cameras configured for capturing medical/surgical specimen
two lenses wherein each lens is coupled to one of the two digital cameras and configured for magnifying an image of a medical/surgical specimen object,
a camera mount platform onto which the two digital cameras and the coupled lens are attached,
two camera mount brackets wherein each one camera mount bracket secures one of the cameras to the camera mount platform with holding fasteners,
two lens mount brackets wherein each one lens mount bracket secures one of the lenses to the camera mount platform with holding fasteners, and
a z-axis leadscrew assembly comprising:
a z-axis leadscrew adapted for rotating,
a z-axis leadscrew block having a threaded, circular opening threaded onto the leadscrew,
a first bearing secured at one end the z-axis lead screw to permit rotation of the leadscrew,
a second bearing secured an opposing end of the z-axis lead screw to permit rotation of the leadscrew, and
a z-axis motor coupled to the second bearing and secured t such that when the z-axis motor receives power the z-axis lead screw is rotated to adjust the camera mount platform, and
a monitor coupled to the two cameras for displaying images from the two cameras;
attaching the microscope camera system to a rigid frame;
placing a sample comprising a set of equally sized and spaced vertical lines on a sample stand attached to the rigid frame;
activating the cameras of microscope camera system to capture and first and second image from the two cameras;
overlap and superimpose the first and second images from the two cameras on the monitor;
loosen the fasteners securing the two cameras and lenses to the camera mount;
adjusting the cameras until the images from the two cameras are aligned as overlapped and superimposed; and tighten the fasteners to secure the two cameras and two lenses.

8. The method of claim 7 further comprising steps equalizing color/brightness of the two cameras of the 3D microscope system, wherein the steps of equalizing the color/brightness comprises the steps of:
a) placing a photospectrometer on a display area of the monitor;
b) connecting the photospectrometer to an image processor connected to the 3D microscope system;
c) placing a sample with a color palette on the sample stand;
d) capturing the images from the two cameras;
e) placing the two images from the two cameras side-by-side on the display area of the monitor;
f) activating the photospectrometer to capture color/brightness measurements;
g) transferring the color/brightness measurements to the image processor wherein the image processor executes a program process for adjusting color brightness setting of the two cameras;
h) executing the program process for determining a difference between the color/brightness setting of the two cameras;
i) comparing a difference of the color/brightness measurements of the two cameras with a threshold to determine if the color/brightness measurements sufficiently match;
j) when the color/brightness measurement difference is greater than the threshold, adjusting a color/brightness parameter of the two cameras;
k) performing steps f) through j until the color/brightness measurement difference is less than the threshold; and
l) saving the color/brightness parameter adjustment data in a non-volatile memory of the image processor.

9. The method of claim 7 further comprising steps eliminating image distortion from toe-in of the cameras, wherein the steps of eliminating image distortion comprises the steps of:
placing a sample of equally spaced grid lines on the sample stage;
adjusting the focus of the two cameras;
capturing the images from the two cameras;
comparing the two images for distortion;
performing a warp function on the two images to achieve perfect alignment of the two images;
saving the alignment data in non-volatile memory of the image processor;
rectifying the images to eliminate keystone distortion; and
saving the keystone distortion elimination data to the non-volatile memory of the image processor.

10. A method for converting 2D microscope image data from at least two cameras of a medical/surgical microscope system into 3D microscope image data for display on a 3D monitor:
activating the at least two cameras for capturing at least two frames of image data;
formatting the at least two frames for resizing or converting the at least two images to a 3D monitor conforming format;
calibrating display alignment of the at least two image frames based on alignment correction data retained in non-transitory memory of an image processor connected between the 3D microscope system and the 3D monitor;
rectifying keystone distortion of the at least two image frames resulting from toe-in from the at least two cameras base on keystone distortion correction data retained in non-transitory memory of the image processor connected between the 3D microscope system and the 3D monitor;
equalizing color/brightness differences among the at least two cameras based on color brightness correction data correction data retained in non-transitory memory of an image processor connected between the 3D microscope system and the 3D monitor;
combining the at least two image frames from the at least two cameras to merge the at least two image frames of the at least two cameras to create an image that conforms to the 3D image formats of the 3D monitor; and
transferring the 3D image frame to the 3D monitor.

11. The method of claim 10 wherein the medical/surgical microscope system comprises:
a camera mount platform onto which the at least two digital cameras are attached;
at least two camera mount brackets wherein each camera mount bracket secures one of the cameras to the camera mount platform with holding fasteners; and a z-axis leadscrew assembly comprising:
  a z-axis leadscrew adapted for rotating,
  a z-axis leadscrew block having a threaded, circular opening threaded onto the leadscrew,
  a first bearing secured at one end the z-axis lead screw to permit rotation of the leadscrew,
  a second bearing secured an opposing end of the z-axis lead screw to permit rotation of the leadscrew, and
  a z-axis motor coupled to the second bearing and secured t such that when the z-axis motor receives power the z-axis lead screw is rotated to adjust the camera mount platform; and
  a rigid frame onto which the camera platform is attached to secure the at least two cameras on the camera platform.

12. The method of claim 11 wherein the step of calibrating display alignment comprises the steps of:
  placing a sample comprising a set of equally sized and spaced vertical lines on a sample stand attached to the rigid frame;
  activating the at least two cameras to capture and the at least two images from the at least two cameras;
  overlapping and superimposing the at least two images from the at least two cameras on the 3D monitor;
  loosening the fasteners securing the at least two cameras to the camera mount;
  adjusting the at least two cameras until the images from the at least two cameras are aligned as overlapped and superimposed; and
  tightening the fasteners to secure the at least two cameras.

13. The method of claim 12 where the step of equalizing color/brightness of the two cameras of the 3D microscope system comprises the steps of:
  a) placing a photospectrometer on a display area of the 3D monitor;
  b) connect the photospectrometer to an image processor connected to the 3D microscope system;
  c) place a sample with a color palette on the sample stand;
  d) capture the images from the at least two cameras;
  e) place the at least two images from the at least two cameras side-by-side on the display area of the 3D monitor;
  f) activate the photospectrometer to capture color/brightness measurements;
  g) transfer the color/brightness measurements to the image processor wherein the image processor executes a program process for adjusting color brightness setting of the at least two cameras;
  h) executing the program process for determining a difference between the color/brightness setting of the at least two cameras;
  i) comparing difference of the color/brightness measurements of the at least two cameras with a threshold to determine if the color/brightness measurements sufficiently match;
  j) when the color/brightness measurement difference is greater than the threshold, adjusting a color/brightness parameter of the at least two cameras;
  k) performing steps f) through j until the color/brightness measurement difference is less than the threshold; and
  l) saving the color/brightness parameter adjustment data in a non-volatile memory of the image processor.

14. The method of claim 12 wherein the steps of rectifying keystone image distortion from toe-in of the at least two cameras comprises the steps of:
  placing a sample of equally spaced grid lines on the sample stage;
  adjusting the focus of the at least two cameras;
  capturing the images from the at least two cameras;
  comparing the at least two images for distortion;
  performing a rectification function on the at least two images to eliminate keystone distortion from the at least two images;
  saving keystone distortion elimination data to the non-volatile memory of the image processor.

15. The method of claim 12 wherein in the step of combining the at least two image frames to form the 3D image frame comprises the step of interspersing pixels of that least two image frames into a single or sequence of frames such that the at least two image frames are organized as sequentially or temporally multiplexed pixels of the at least two image frames, organized as side-by-side arranged pixels of the at least two image frames, organized as top-and-bottom arranged pixels of the at least two image frames, organized as line-by-line arranged pixels of the at least two image frames, organized as a quincunx arranged checkerboard of the pixels of the at least two image frames, or organized in any suitable arrangement of pixels of the at least two image frames.

* * * * *